US009963497B2

(12) United States Patent
Kaempfer et al.

(10) Patent No.: US 9,963,497 B2
(45) Date of Patent: May 8, 2018

(54) REDUCTION OF INFLAMMATORY DISEASE SYMPTOMS BY SHORT PEPTIDES THAT INHIBIT SIGNALING THROUGH CD28

(71) Applicants: YISSUM RESEARCH DEVELOPMENT COMPANY OF THE HEBREW UNIVERSITY OF JERUSALEM LTD, Jerusalem (IL); ATOX BIO LTD., Ness Ziona (IL)

(72) Inventors: Raymond Kaempfer, Jerusalem (IL); Anat Shirvan, Kfar-Saba (IL); Gila Arad, Mevasseret Zion (IL)

(73) Assignees: YISSUM RESEARCH DEVELOPMENT COMPANY OF THE HEBREW UNIVERSITY OF JERUSALEM LTD, Jerusalem (IL); ATOX BIO LTD., Ness Ziona (IL)

( * ) Notice: Subject to any disclaimer, the term of this patent is extended or adjusted under 35 U.S.C. 154(b) by 0 days. days.

(21) Appl. No.: 15/035,571

(22) PCT Filed: Dec. 7, 2014

(86) PCT No.: PCT/IL2014/051067
  § 371 (c)(1),
  (2) Date: May 10, 2016

(87) PCT Pub. No.: WO2015/083173
  PCT Pub. Date: Jun. 11, 2015

(65) Prior Publication Data
  US 2016/0289295 A1  Oct. 6, 2016

Related U.S. Application Data

(60) Provisional application No. 61/924,869, filed on Jan. 8, 2014, provisional application No. 61/912,631, filed on Dec. 6, 2013.

(51) Int. Cl.
  *C07K 14/705* (2006.01)
  *A61K 38/04* (2006.01)
  *A61K 38/17* (2006.01)
  *A61K 45/06* (2006.01)
  *A61K 38/00* (2006.01)

(52) U.S. Cl.
  CPC .... *C07K 14/70521* (2013.01); *A61K 38/1774* (2013.01); *A61K 45/06* (2013.01); *A61K 38/00* (2013.01)

(58) Field of Classification Search
  None
  See application file for complete search history.

(56) References Cited

U.S. PATENT DOCUMENTS

| 8,535,672 | B2 * | 9/2013 | Kaempfer | C07K 14/70521 424/144.1 |
| 9,546,207 | B2 * | 1/2017 | Kaempfer | C07K 14/70521 |
| 2005/0191296 | A1 * | 9/2005 | Kaempfer | C07K 14/70521 424/144.1 |
| 2011/0097339 | A1 * | 4/2011 | Holmes | C07K 16/2818 424/158.1 |
| 2013/0078236 | A1 * | 3/2013 | Mary | C07K 16/2818 424/133.1 |

FOREIGN PATENT DOCUMENTS

| DE | 102012008730 | 6/2013 |
| WO | 2004/087196 | 10/2004 |
| WO | 2004/087754 | 10/2004 |
| WO | 2013/108193 | 7/2013 |

OTHER PUBLICATIONS

Harari et al., Allergy 65 (2010) 537-553.*
Maiorino et al., Endocrine May 26, 2016. [Epub ahead of print], 6 pages.*
Mirzoeva et al. (PLoS ONE, 2014, vol. 9, issue 7, p. 1-8).*
Harari et al., Allergy 2010; 65: 537-553.*
Soper D. "Pelvic Inflammatory Disease" Merck Manual 2017 (accessed online on Apr. 4, 2017 at http://www.merckmanuals.com/professional/gynecology-and-obstetrics/vaginitis,-cervicitis,-and-pelvic-inflammatory-disease-pid/pelvic-inflammatory-disease-pid) 8 pages.*
Arad, et al., Binding of Superantigen Toxins into the CD28 Homodimer Interface is Essential for Induction of Cytokine Genes That Mediate Lethal Shock, PLoS Biology, Sep. 2011, pp. 1-14, vol. 9, issue 9.
Arad, et al., Superantigen antagonist protects against lethal shock and defines a new domain for T-cell activation, Nature Medicine, Apr. 2000, pp. 414-421, vol. 6, No. 4.
Bulger, et al., A Novel Drug for Treatment of Necrotizing Soft-Tissue Infections, A Randomized Clinical Trial, JAMA Surg., 2014, pp. 528-536, vol. 149(6).
Evans, et al., Crystal structure of a soluble CD28-Fab complex, Nature Immunology, Mar. 2005, pp. 271-279, vol. 6, No. 3.
Francois, et al., Inflammation and Immunity in Radiation Damage to the Gut Mucosa, BioMed Research International, 2013, pp. 1-9, vol. 2013.
Kaempfer, et al., CD28: Direct and Critical Receptor for Superantigen Toxins, Toxins, 2013, pp. 1531-1542, vol. 5.
Kapsogeorgou, et al., A Novel B7-2 (CD86) Splice Variant with a Putative Negative Regulatory Role, The Journal of Immunology, 2008, pp. 3815-3823, vol. 180.
Petersen, et al., New Targets for the Modulation of Radiation Response—Selective Inhibition of the Enzyme Cyclooxygenase 2, Curr. Med. Chem.—Anti-Cancer Agents, 2003, pp. 354-359, vol. 3.
Ramachandran, et al., A Peptide Antagonist of CD28 Signaling Attenuates Toxic Shock and Necrotizing Soft-Tissue Infection Induced by *Streptococcus* pyogenes, J. Infect. Dis., 2013, pp. 1869-1877, vol. 207.

(Continued)

*Primary Examiner* — Ilia I Ouspenski
(74) *Attorney, Agent, or Firm* — Browdy and Neimark, PLLC

(57) ABSTRACT

The present disclosure relates to a method for the treatment of a non-pathogen associated inflammatory disorders in a subject in need thereof, comprising administering to said subject an isolated peptide which specifically binds to an amino acid sequence within the dimer interface of a T cell costimulatory pathway member, particularly the T cell costimulatory pathway members CD28 and CTLA4. The present disclosure also relates to pharmaceutical compositions comprising the isolated peptide and to use of the peptide in treating of a non-pathogen associated inflammatory disorders.

22 Claims, 16 Drawing Sheets

(56) References Cited

OTHER PUBLICATIONS

Schwartz, et al., Structural basis for co-stimulation by the human CTLA-4/B7-2 complex, Nature, Mar. 2001, pp. 604-608, vol. 410.
Srinivasan, et al., Suppression of Experimental Autoimmune Encephalomyelitis Using Peptide Mimics of CD28, The Journal of Immunology, 2002, pp. 2180-2188, vol. 169.
Rock et al. The inflammatory response to cell death. Annu Rev Pathol., 3:99-126, Review (2008).
Karnatovskaia et al., Sepsis: a review for the neurohospitalist. Neurohospitalist, 2(4):144-53 (2012).
Van Der Poll et al., Host-pathogen interactions in sepsis. Lancet Infect Dis., 8(1):32-43 (2008).
Schaue et al., Cytokines in radiobiological responses: a review, Radiat Res., 178(6):505-23 (2012).
Zhao et al., Inflammation and chronic oxidative stress in radiation-induced late normal tissue injury: therapeutic implications, Curr Med Chem., 16(2):130-43 (2009).
Singh et al., Nf-κB as a key player in regulation of cellular radiation responses and identification of radiation countermeasures. Discoveries, 3 (1), e35 (2015).
Park et al., RAK4 as a molecular target in the amelioration of innate immunity-related endotoxic shock and acute liver injury by chlorogenic acid, J Immunol., 194(3):1122-30 (2015).
Mirzoeva et al, Single Administration of p2TA (AB103), a CD28 Antagonist Peptide, Prevents Inflammatory and Thrombotic Reactions and Protects against Gastrointestinal Injury in Total-Body Irradiated Mice. PLoS One 9(7): el 01161. doi:10.1371/journal.pone.0101161 (2014).
Hekim et al., Radiation triggering immune response and inflammation, Cancer Lett, 368(2):156-63. Review (2015).
Holzheimer, Antibiotic induced endotoxin release and clinical sepsis: a review, J Chemother., 1(1):159-72 (2001).
Lorenzo et al., Lung inflammatory pattern and antibiotic treatment in pneumonia, Respir Res., 16:15 (2015).

\* cited by examiner

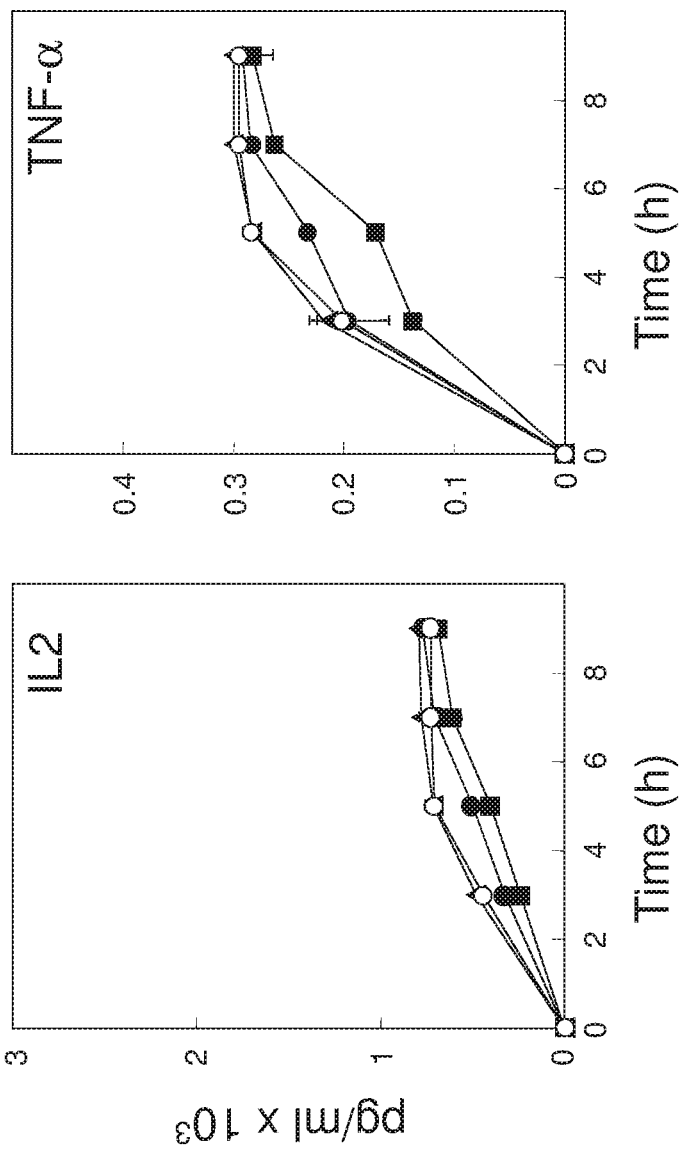

Fig. 2A
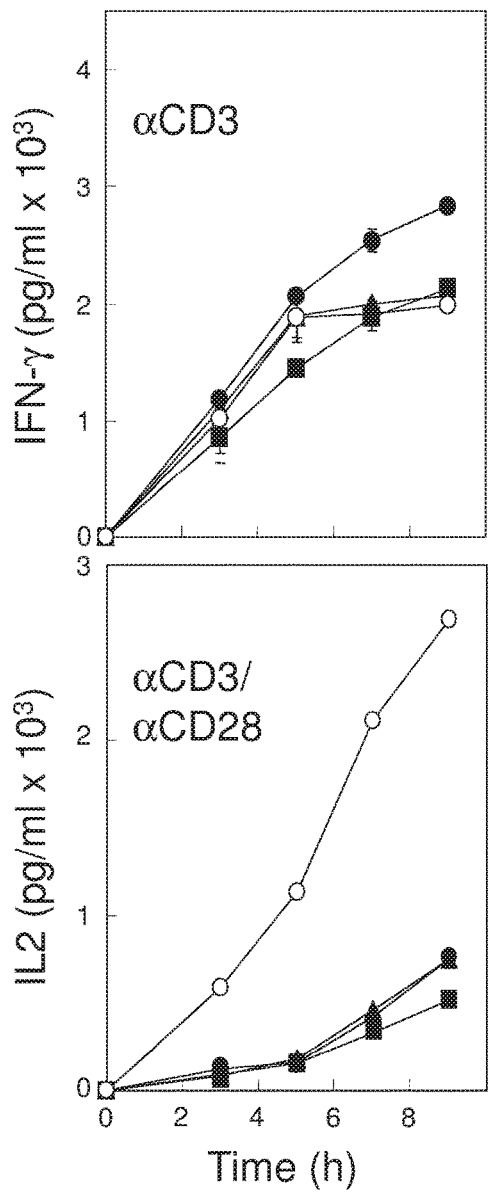
Fig. 2C
Fig. 2B
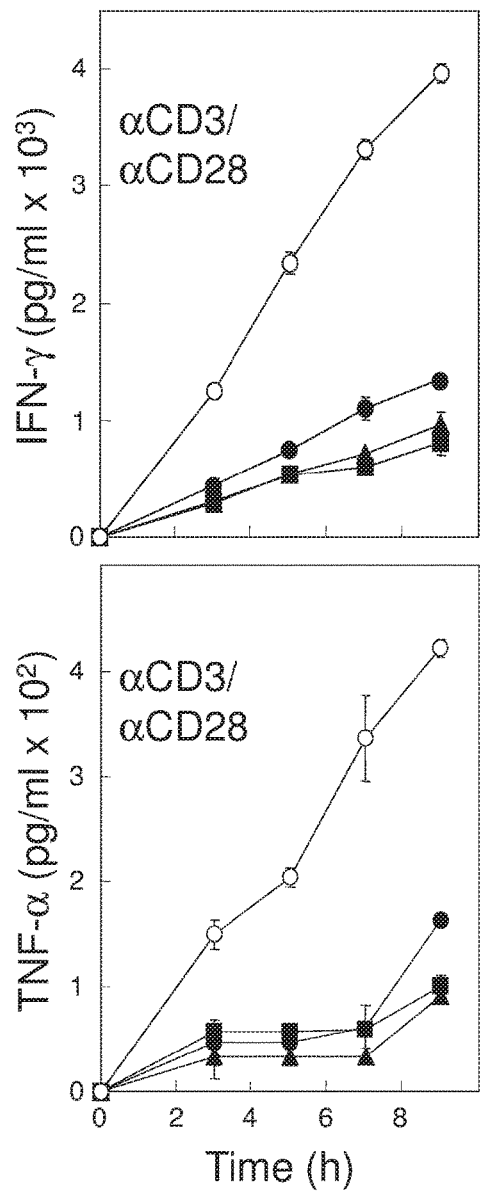
Fig. 2D

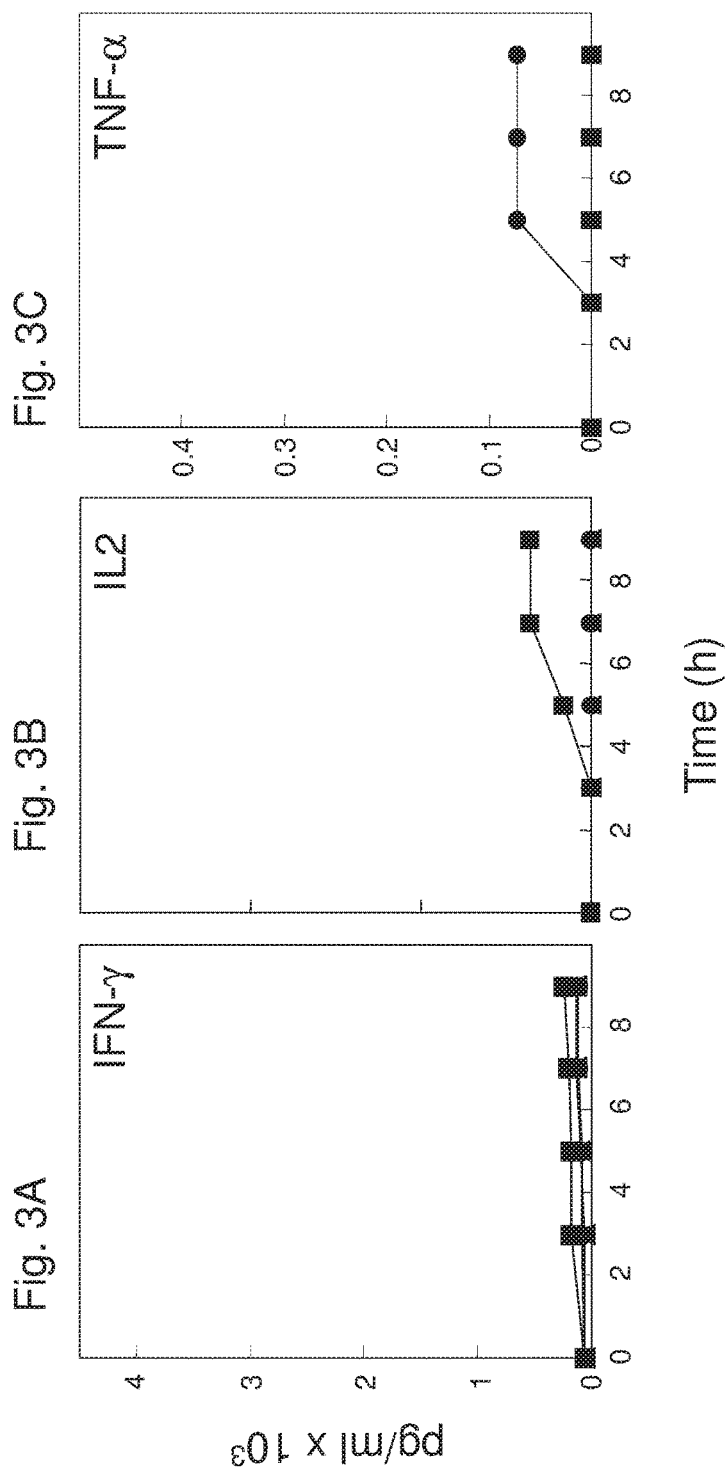

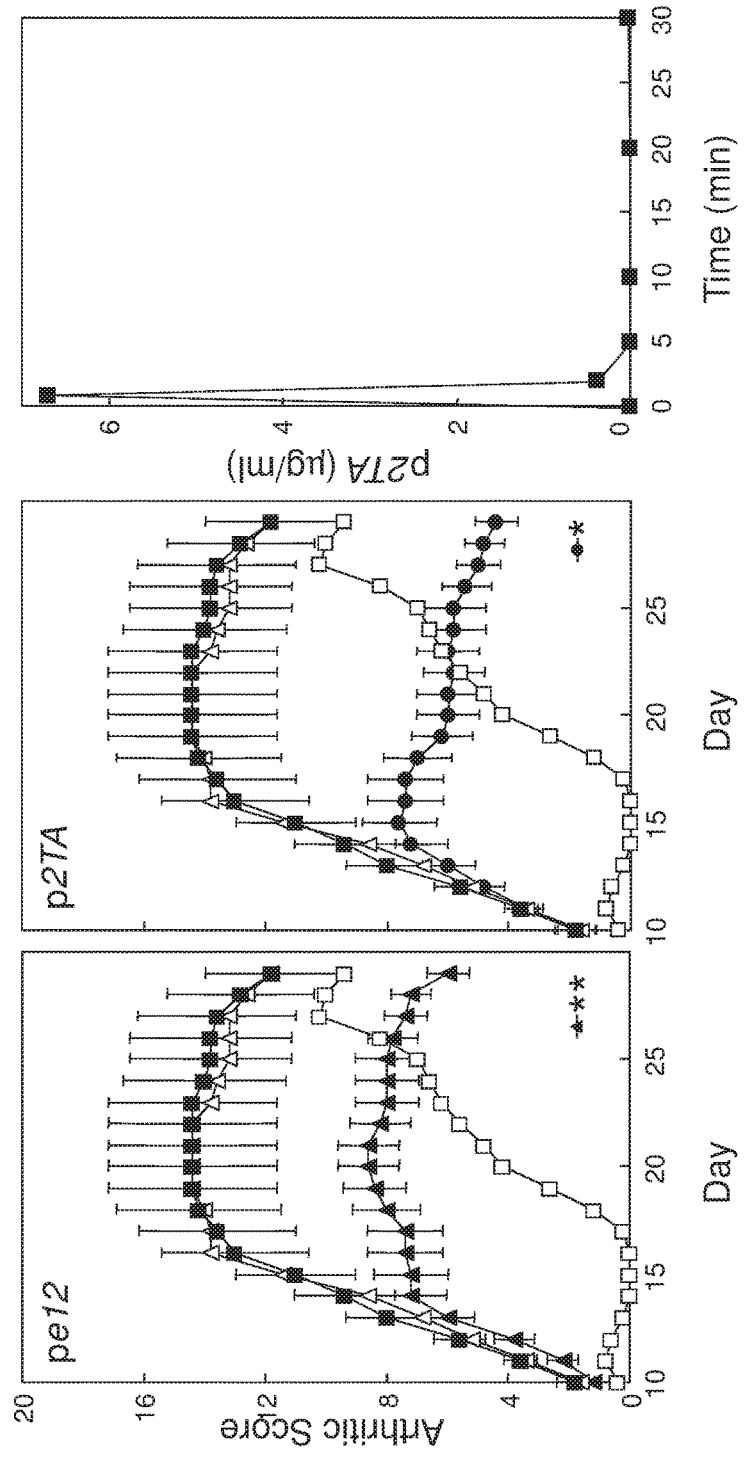

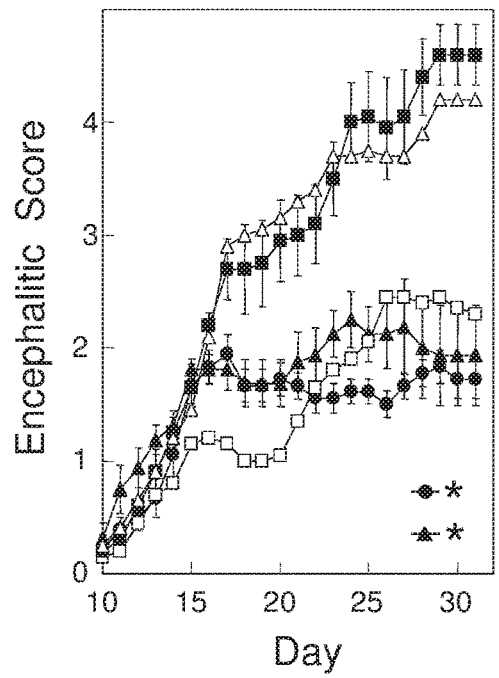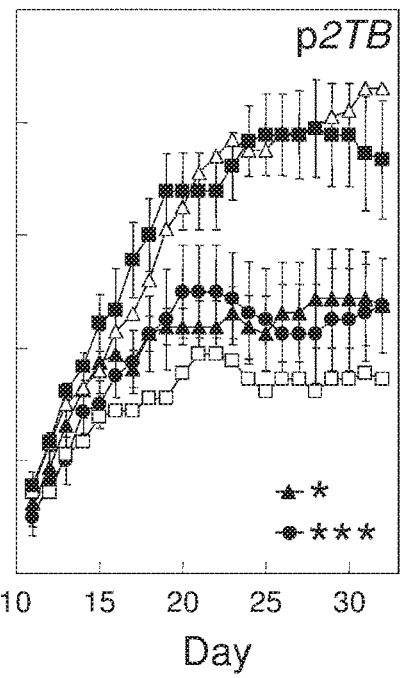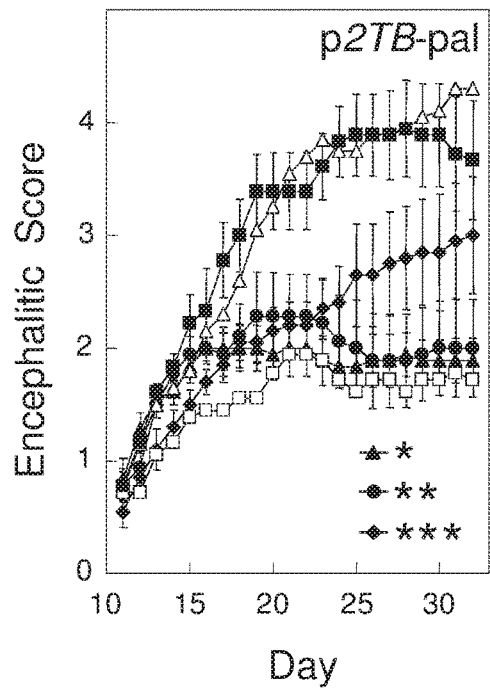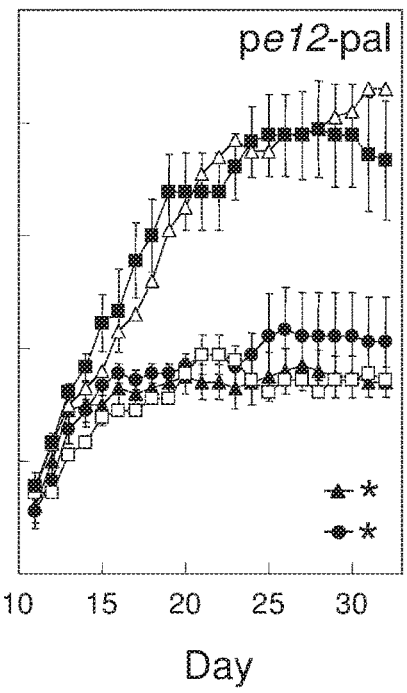

|  | BALB/c | A/J |
|---|---|---|
| C | Fig. 14A 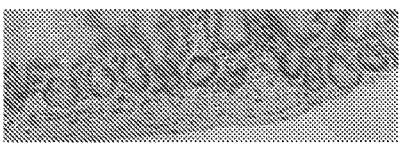 | Fig. 14E 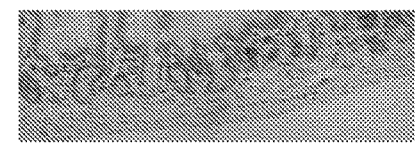 |
| P | Fig. 14B 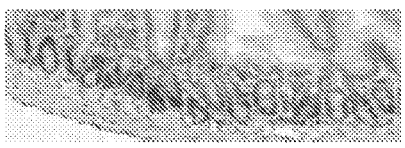 | Fig. 14F 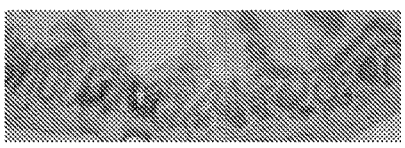 |
| R | Fig. 14C 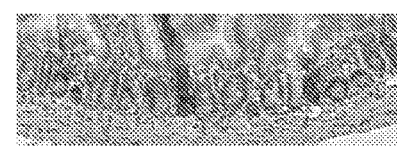 | Fig. 14G 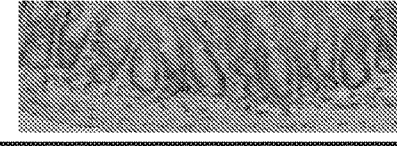 |
| RP | Fig. 14D  | Fig. 14H 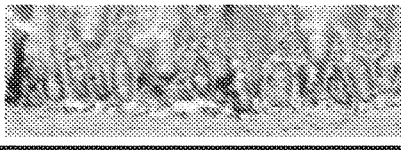 |

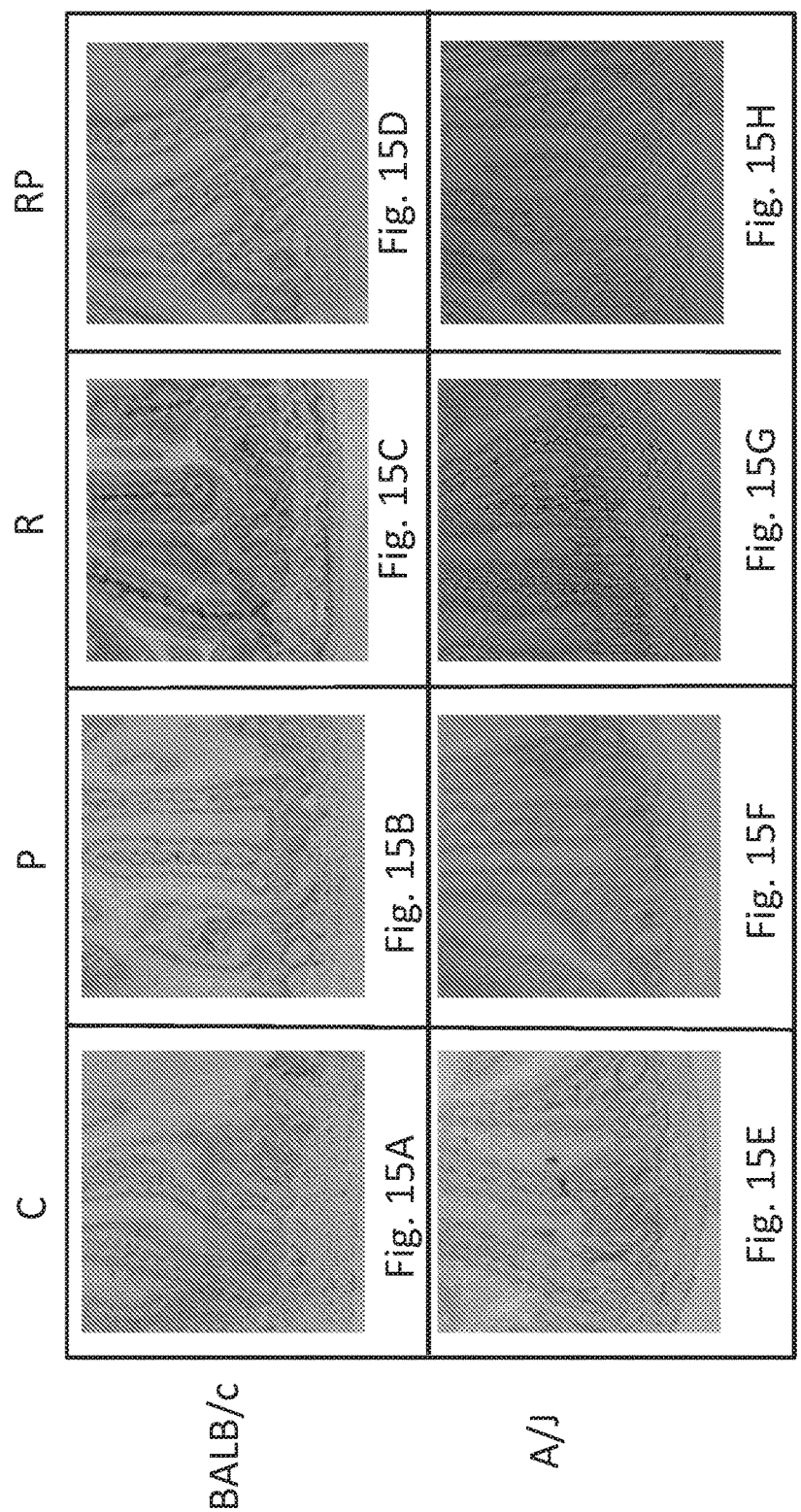

REDUCTION OF INFLAMMATORY DISEASE SYMPTOMS BY SHORT PEPTIDES THAT INHIBIT SIGNALING THROUGH CD28

TECHNOLOGICAL FIELD

The present disclosure generally relates to a method of treating inflammatory diseases and symptoms associated therewith. In particular, the present disclosure relates to the use of short peptides that inhibit signaling through CD28.

BACKGROUND ART

References considered to be relevant as background to the presently disclosed subject matter are listed below:
[1] Francois A, Milliat F, Guipaud O, Benderitter M. Inflammation and immunity in radiation damage to the gut mucosa. Biomed Res Int.; 2013:123241.
[2] Arad G, Levy R, Hillman D, Kaempfer R. Superantigen antagonist protects against lethal shock and defines a new domain for T-cell activation. Nat Med. 2000; 6:414-21.
[3] Arad G, Levy R, Nasie I, Hillman D, Rotfogel Z, Barash U, et al. Binding of Superantigen Toxins into the CD28 Homodimer Interface Is Essential for Induction of Cytokine Genes That Mediate Lethal Shock. PLoS Biol. 2011. page e1001149.
[4] Ramachandran G, Tulapurkar M E, Harris K M, Arad G, Shirvan A, Shemesh R, et al. A peptide antagonist of CD28 signaling attenuates toxic shock and necrotizing soft-tissue infection induced by *Streptococcus pyogenes*. J Infect Dis. 2013; 207:1869-77.
[5] Kaempfer R, Arad G, Levy R, Hillman D, Nasie I, Rotfogel Z. CD28: Direct and Critical Receptor for Superantigen Toxins. Toxins (Basel). 2013; 5:1531-42.
[6] Petersen C, Baumann M, Petersen S. New targets for the modulation of radiation response-selective inhibition of the enzyme cyclooxygenase 2. Curr Med Chem Anticancer Agents. 2003; 3:354-9.
[7] Bulger E, Maier R, Sperry J, Joshi M, Henry S, Moore F A, et al. A novel drug for treatment of necrotizing soft tissue infections: Results of a Phase 2a randomized controlled trial of AB103, a CD28 co-stimulatory receptor antagonist. JAMA J Am Med Assoc Surg. 2014; 149, 528-536.
[8] WO 2013/108193.
[9] Srinivasan M, Gienapp I E, Stuckman S S, Rogers C J, Jewell S D, Kaumaya P T, Whitacre C C. (2002) Suppression of experimental autoimmune encephalomyelitis using peptide mimics of CD28. J Immunol. 169:2180-2188.
[10] Kapsogeorgou, E. K., Moutsopoulos, H. M. & Manoussakis, M. N. A novel B7-2 (CD86) splice variant with a putative negative regulatory role. J. Immunol. 180, 3815-3823 (2008).
[11] Evans, J. E. et al. Nat Immun (2005) 6:271-279.
[12] Schwartz J C et al. Nature (2201) 410:604-608

Acknowledgement of the above references herein is not to be inferred as meaning that these are in any way relevant to the patentability of the presently disclosed subject matter.

BACKGROUND

Inflammation is a protective response that is intended to eliminate the initial cause of cell injury, as well as any necrotic cells and tissues resulting from the original insult, and to initiate the process of repair. Chronic inflammation might lead to a host of diseases, and is therefore normally closely regulated.

Chronic inflammatory diseases such as rheumatoid arthritis (RA) and multiple sclerosis (MS) are associated with aberrant cytokine expression patterns, in which the Th1 cytokines play an important role. Among these, tumor necrosis factor (TNF-α), interferon-γ (IFN-γ) and interleukin-2 (IL2) are cytokines that exhibit synergism in their immunopotentiating and immunomodulating activities and contribute to inflammatory disease symptoms.

In particular, exposure to ionizing radiation (IR) promotes both inflammatory reactions and immune system imbalance. Radiation-induced acute inflammatory responses have been shown to activate multiple pro-inflammatory cytokines and inhibit anti-inflammatory cytokines; thus, cytokines are often used to modulate the effects of IR.

The excessive gastrointestinal (GI) inflammatory response that occurs following radiation is considered one of the drivers of multiple organ failure induced by IR (2, 3). For example, pulmonary injury may be an abscopal effect of GI irradiation injury. Therefore, modulating radiation induced inflammatory reactions, especially in the GI tract may also have significant effects on other parts of the irradiated body.

The inflammatory cytokine signal relies not only on antigenic presentation but is fully dependent on costimulatory signaling, in which Cluster of differentiation 28 (CD28) has a key function.

The CD28 antigen is expressed on T cells and is required for their activation as well as the survival and expansion of the peripheral blood T cells. Stimulation through CD28 can provide a potent co-stimulatory signal to T cells for the production of multitude of pro-inflammatory mediators, including IL-6 and fibrinogen, both involved in the progression of tissue injury. It has been reported that short peptides can prevent CD28 signaling induced by superantigen toxins (2, 3 and 8) or streptococcal infection (4). Specifically, it has been shown that a member of the above short peptides, namely the peptide p2TA, an octapeptide mimetic of the CD28 homodimer, prevents the engagement of CD28 by superantigens in vivo, thus averting T cell activation leading to protection from lethal toxic shock caused by an excessive inflammatory response (3, 5). At the same time, p2TA leaves the Th2-cytokine based humoral immune response intact (3, 4).

GENERAL DESCRIPTION

The present disclosure provides an isolated peptide which specifically binds to the crystallographic homodimer interface of CD28 and functional fragments and derivatives thereof, or a pharmaceutical composition comprising the same, for use in a method for the treatment of a non-pathogen associated inflammatory disorder.

The said isolated peptide has a binding affinity for the crystallographic homodimer interface of CD28 characterized by $K_D$ lower than 30 micromolar, more specifically $K_D$ of from about 0.1 to about 30 micromolar.

The said isolated peptide inhibits non-pathogen induced inflammatory response, as determined by a reduction in the level of at least one of the inflammatory cytokines IL2, interferon-γ (IFN-γ) and tumor necrosis factor-α (TNF-α) and/or by reduction in the level of cyclooxygenase 2 (cox-2) and/or by a decrease in the number of F4/80-positive cells.

The said isolated peptide can have an amino acid sequence that corresponds to a region of from 6 to 14 consecutive amino acid residues within human CD28 (SEQ ID NO: 1) or within human CTLA4 (SEQ ID NO: 2), which region harbors one or more amino acid residues of the crystallographic homodimer interface of human CD28, respectively human CTLA4, and said peptide and its functional fragments and derivatives maintain the ability to bind to said crystallographic homodimer interface of CD28 at a binding affinity characterized by a $K_D$ lower than 30 micromolar, more specifically $K_D$ of from about 0.1 to about 30 micromolar, and to inhibit non-pathogen induced inflammatory response, as determined by a reduction in the level of at least one of the inflammatory cytokines IL2, interferon-γ (IFN-γ) and tumor necrosis factor-α (TNF-α) and/or by reduction in the level of cyclooxygenase 2 (cox-2) and/or by a decrease in the number of F4/80-positive cells. The said region of human CD28 comprises amino acid residues 10-15 or 116-121 of SEQ ID NO:1, and said region of CTLA4 comprises amino acid residues 10-15 and 115-120 of SEQ ID NO: 2.

Specifically disclosed peptides in accordance with the present disclosure are peptides consisting of the amino acid sequences His Val Lys Gly Lys His Len Cys Pro (denoted by SEQ ID NO: 3), Ser Pro Met Len Val Ala Tyr Asp (denoted by SEQ ID NO: 4), His Lys Gly Len Asp Ser Ala Val (denoted by SEQ ID NO: 5), Tyr Val Asn Gln Thr Asp Ile Tyr (denoted by SEQ ID NO:6), Asn Gly Thr Ile Ile His Val Lys Gly (denoted by SEQ ID NO: 7), Tyr Val Ile Asp Pro Glu Pro Cys Pro (denoted by SEQ ID NO: 8), Pro Ala Val Val Len Ala Ser Ser (denoted by SEQ ID NO: 9), and their functional derivatives.

Also disclosed are peptides selected from the group consisting of the amino acid sequences Tyr Asn Lys Lys Lys Ala Thr Val Gln Glu Leu Asp (denoted by SEQ ID NO: 10), Val Gln Tyr Asn Lys Lys Lys Ala Thr Val Gln Glu Leu Asp (denoted by SEQ ID NO: 11), Ser His Phe Thr His Asn Arg His Gly His Ser Thr (denoted by SEQ ID NO: 12), Phe His Lys His Lys Asn Pro Gly Ser Pro Ile Ile (denoted by SEQ ID NO: 14) and Trp His Ala His Pro His Lys Lys Pro Val Val Ala (denoted by SEQ ID NO: 13) and functional derivatives thereof.

In a specific embodiment, the isolated peptide comprises the amino acid sequence Ser Pro Met Len Val Ala Tyr Asp denoted by SEQ ID NO. 4 or the amino acid sequence (D-Ala) Ser Pro Met Len Val Ala Tyr Asp (D-Ala) denoted by SEQ ID NO. 47.

In another specific embodiment, the said peptide comprises the amino acid sequence Pro Ala Val Val Leu Ala Ser Ser (denoted by SEQ ID NO: 9), (D-Ala)PAVVLASS(D-Ala) (denoted by SEQ ID NO: 48) and (palmitoyl-lysine) Pro Ala Val Val Len Ala Ser Ser (D-Ala) (denoted by SEQ ID NO: 50).

Still further peptides in accordance with the present disclosure comprise the amino acid sequence Ser His Phe Thr His Asn Arg His Gly His Ser Thr (denoted by SEQ ID NO: 12), the amino acid sequence (D-Ala) Ser His Phe Thr His Asn Arg His Gly His Ser Thr (D-Ala) (denoted by SEQ ID NO: 49) and the amino acid sequence (palmitoyl-lysine) Ser His Phe Thr His Asn Arg His Gly His Ser Thr D-Ala) (denoted by SEQ ID NO: 51).

In all aspects and embodiments of the present disclosure the said inflammatory disorder to be treated by peptides in accordance with the present disclosure or pharmaceutical compositions comprising the same is any one of radiation-induced inflammation, inflammatory bowel disease (IBD), radiation-induced gastroenteritis, drug-induced inflammation, arthritis, rheumatoid arthritis, osteoarthritis, lupus, myasthenia gravis, multiple sclerosis, adult respiratory distress syndrome (ARDS), asthma, rhinitis, idiopathic pulmonary fibrosis, peritonitis, cardiovascular inflammation, myocardial ischemia, reperfusion injury, atherosclerosis, trauma, diabetes type II, retinopathy, psoriasis, gastrointestinal inflammation, cirrhosis, appendicitis, bursitis, colitis, cystitis, dermatitis, phlebitis, vasculitis, acne vulgaris, and pelvic inflammatory disease.

More specifically, the said drug-induced inflammation is any one of drug-induced hepatitis, drug-induced ocular inflammation, drug-induced gastrointestinal damage, drug-induced acute ulcers, drug-induced renal failure, drug-induced pancreatitis, drug-induced nephritis, chemotherapy-induced inflammation in the gastrointestinal tract and seborrheic keratosis.

In a specific embodiment, the said inflammatory disease or condition is radiation-induced inflammation, which can be systemic and/or at the irradiated site. The said radiation-induced inflammation can be associated with at least one of gastrointestinal tract and spleen inflammation.

In a further embodiment, the present disclosure provides an isolated peptide which specifically binds to the crystallographic homodimer interface of CD28, or a pharmaceutical composition comprising said isolated peptide, for use in a method for the treatment of radiation-induced inflammation.

In all aspects and embodiments of the present disclosure the isolated peptide or pharmaceutical composition for use according to the present disclosure, can be administered by a route selected from the group consisting of intravenous, intramuscular or intraperitoneal administration, intrathecal or subcutaneous injection, oral, intrarectal, intranasal ocular and topical administration.

In all aspects and embodiments of the present disclosure isolated peptide can be administered at an amount of from about 0.05 mg to about 5.0 mg peptide/kg body weight of a subject in need thereof.

In all aspects and embodiments of the present disclosure the said isolated peptide or pharmaceutical composition comprising the same is administered at one or more identical or different treatment periods of one, two, three or four weeks of once daily, once every three days, once every five days or once weekly administrations of said isolated peptide, wherein said treatment periods are consecutive or are set apart from each other by non-treatment intervals of 1 or several days, or 1 or several weeks or 1 or more months. The isolated peptide or pharmaceutical composition comprising the same can be administered at a single dose.

In all aspects and embodiments of the present disclosure the said isolated peptide or pharmaceutical composition comprising the same said administration can be at one or more treatment periods of one, two, three or four weeks of once daily administrations of a therapeutically effective amount of said isolated peptide.

In embodiments of the presently disclosed subject matter, said isolated peptide or pharmaceutical composition is for chronic administration.

In the various aspects and embodiments of the present disclosure the said isolated peptide or pharmaceutical composition comprising the same can be administered once daily, once every three days, once every five days or once weekly.

In embodiments of treatment of radiation-induced inflammation, the said isolated peptide or pharmaceutical composition can be administered to at a suitable time prior to and/or post irradiation. Thus, the said isolated peptide or pharmaceutical composition administered to the subject in need immediately following, or within from about 30 minutes up to any time at which the radiation-induced inflammation persists, whether while the subject is still undergoing radiation therapy, in between radiation therapy treatments or thereafter. The said isolated peptide or pharmaceutical composition can be administered to the subject in need thereof from about 30 minutes to about 60 or 90 minutes, 2, 4, 6, 8, 10, 12, 14, 16, 18, 20, 22, 24, 36, 48, 60 or 72 hours, 4, 5, 6, 7, 14, 32 or 28 days following exposure to said radiation. The said isolated peptide or pharmaceutical composition can be administered to said subject within about 24 hours following exposure to said radiation.

In various aspects or embodiments of the present disclosure, the said isolated peptide or pharmaceutical composition comprising the same can be administered in combination with at least one additional therapeutically active agent. In various embodiments, the said additional therapeutically active agent can be a steroid, a nonsteroidal anti-inflammatory agent or an immunosupressive agent. The said isolated peptide or pharmaceutical composition comprising the same and said at least one additional therapeutically active agent can be administered simultaneously, or at different time points, in identical or different frequencies. For example, the said isolated peptide or pharmaceutical composition comprising the same can be administered prior to or after administration of said at least one additional therapeutically active agent. Further, the said isolated peptide or pharmaceutical composition comprising the same and said at least one additional therapeutically active agent can be administered for different durations of time.

In embodiments related to treatment of, for example, rheumatoid arthritis, said additional therapeutically active agent can be any one of Abatacept, a TNF blocker, an IL-1 blocker, an IL-6 blocker and an Anti CD20 agent or a combination thereof.

In embodiments related to treatment of, for example, multiple sclerosis, said additional therapeutically active agent can be any one of interferon-β, Copaxone and Tysabri or a combination thereof.

In embodiments related to treatment of, for example, radiation-induced gastroenteritis said at least one additional therapeutically active agent can be a chemotherapeutic agent.

BRIEF DESCRIPTION OF THE DRAWINGS

In order to better understand the subject matter that is disclosed herein and to exemplify how it may be carried out in practice, embodiments will now be described, by way of non-limiting example only, with reference to the accompanying drawings, in which:

FIG. 1A-1B: The peptides do not inhibit signaling through CD3. A graph showing levels of the indicated cytokines for human PBMC induced with αCD3 alone (○) or in the presence of 10 μg/ml of (D-Ala)-p2TA-(D-Ala) (▲), p2TB (■), or pe12 (●). At the indicated time points, the levels of IL2 (FIG. 1A) and TNF-α (FIG. 1B) secreted into the culture medium were determined by ELISA (mean+SEM).

FIG. 2A-2D: The peptides inhibit signaling through CD28. A graph showing levels of the indicated cytokines for human PBMC induced with αCD3 (A) or αCD3/αCD28 (B-D) alone (○) or in the presence of 10 μg/ml of (D-Ala)-p2TA-(D-Ala) (▲), p2TB (■), or pe12 (●). At the indicated time points, the levels of IFN-γ (FIG. 2A, FIG. 2B), IL2 (FIG. 2C) and TNF-α (FIG. 2D) secreted into the culture medium were determined by ELISA (mean±SEM).

FIG. 3A-3C: The peptides do not induce a significant Th1 cytokine response. A graph showing levels of the indicated cytokines for human PBMC cultured with 10 μg/ml of (D-Ala)-p2TA-(D-Ala) (▲), p2TB (■), or pe12 (●). At the indicated time points shown, the levels of IFN-γ (FIG. 3A), IL2 (FIG. 3B) and TNF-α (FIG. 3C) secreted into the culture medium were determined by ELISA.

FIG. 6A: Effect of p2TA on binding of B7-2 to cell-surface CD28. A western blot analysis (upper panel) and the quantification thereof (lower bar graph) of HEK293T cells transfected to express cell-surface CD28 or an empty vector (EV) that were incubated with soluble B7-2 in the absence or in the presence of (D-Ala)-p2TA-(D-Ala) at the indicated concentrations (error bars, s.e.m.; n=3). The right panel is a schematic outline of the experimental design.

FIG. 6B: Effect of p2TA on binding of CD28 to cell-surface B7-2. A western blot analysis (upper panel) and the quantification thereof (lower bar graph) of HEK293T cells transfected to express cell-surface B7-2 or an empty vector that were incubated with soluble CD28 in the absence or presence of p2TA at the indiated concentrations (error bars, s.e.m.; n=3). The right panel is a schematic outline of the experimental design.

FIG. 6C: p2TA attenuates intercellular B7-2/CD28 synapse formation. A bar graph showing intercellular B7-2/CD28 synapse formation scored using flow cytometry to quantitate the percentage of doubly labeled cells (error bars, s.e.m.; n=3) in an assay performed with HEK293T cells transfected to express CD28/GFP fusion protein (green label) incubated with HEK293T cells transfected to express B7-2/Cherry fusion protein (red label), in the absence or in the presence of (D-Ala)-p2TA-(D-Ala) at the indicated concentrations. As negative control served B7-2C/Cherry, which lacks the ability to bind CD28. The right panel is a schematic outline of the experimental design.

FIG. 6D-FIG. 6H: Contour plots for representative experiments. In FIG. 6C, upon incubation of cells expressing CD28/GFP with cells expressing B7-2/Cherry (d-g) or B7-2C/Cherry (h). Incubation was in the absence (d,h) or presence of p2TA at 0.1 (e), 0.3 (f) or 1 μg ml$^{-1}$ (g). Percent doubly labeled cells in upper right quadrant is denoted.

FIG. 8A-8B: The peptides reduce symptoms of adjuvant arthritis. Graphs showing arthritic score of arthritis induced in rats (n=5 per group). Symptoms were observed from day 10, scoring 16 joints on 4 legs (■). Dexamethasone (DEXA)

was injected daily during days 10-15. PBS (Δ), 100 μg (D-Ala)-p2TA-(D-Ala) (●)(FIG. 8A) or pe12 (▲)(FIG. 8B) were injected on each of days 1-15. Treatments were terminated on day 15 and symptoms monitored through day 29 (mean±SEM). (*) P<0.001, (**) P=0.004, difference between peptide and untreated groups.

FIG. 9: Pharmacokinetics of p2TA. A graph showing a variation in p2TA at the indicated time points. The peptide (D-Ala)-p2TA-(D-Ala) was injected IV at zero time; at times thereafter, mice (n=3) were sacrificed and the serum level of (D-Ala)-p2TA-(D-Ala) was determined by reverse phase liquid chromatography with mass spectrometric detection. Mean level is shown.

Figures 10A, 10B:
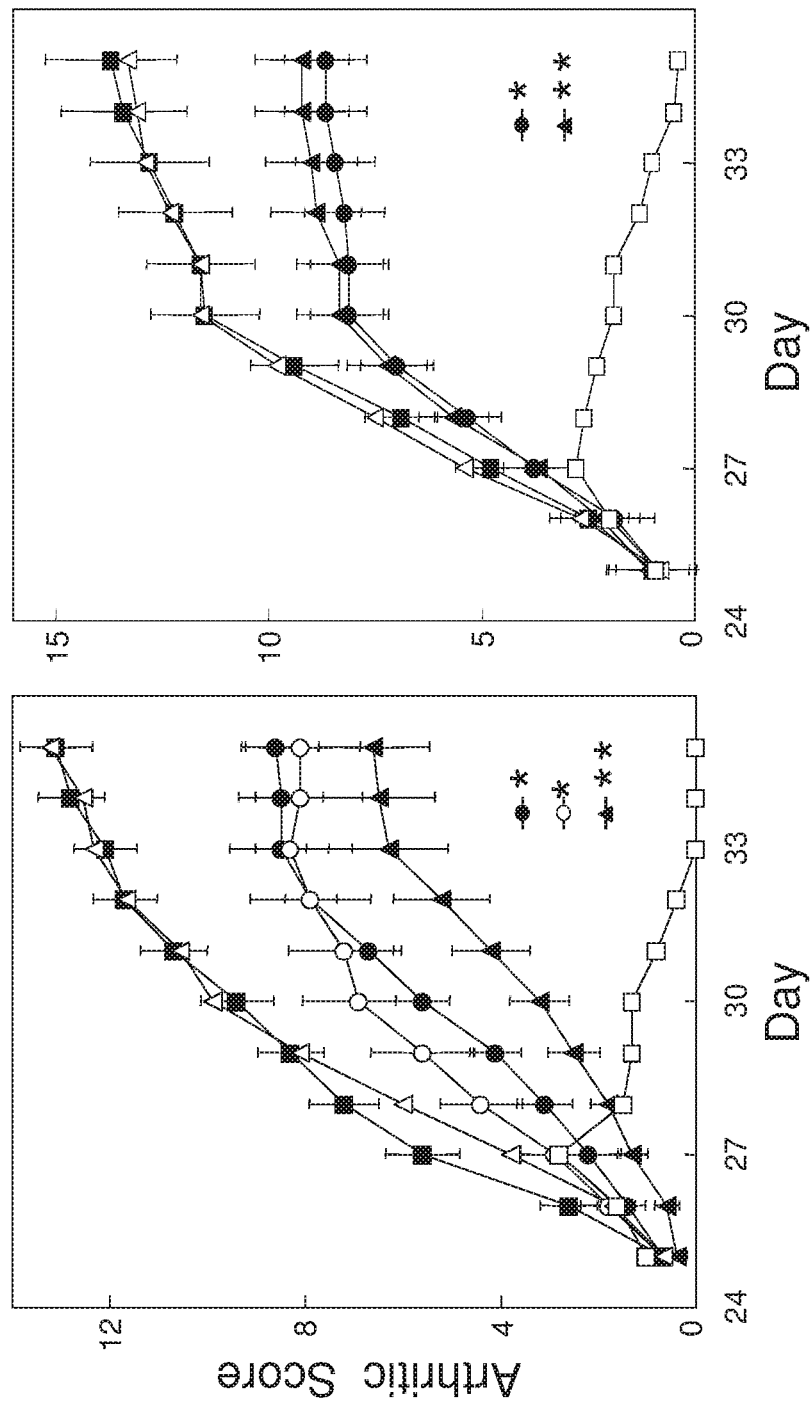

FIG. 10A-10B: The peptides reduce symptoms of collagen-induced arthritis. Graphs showing arthritic score of arthritis induced in mice (n=10 per group) by injecting bovine Type II collagen in complete Freund's adjuvant on days 0 and 21. Symptoms were observed from day 25, scoring 16 joints on 4 legs (■)(mean+SEM) and the mice were treated by (FIG. 10A) Dexamethasone (DEXA) at 100 μg (□), PBS (Δ) or 10 μg p2TA (▲) injected daily from disease onset (days 25-34) or 100 μg p2TB (●) or p2TB-pal (○) injected once every 3 days starting on day 25. Values are shown for days 25-35 (mean±SEM). (*) P<0.001, (**) P=0.015, difference between peptide and untreated groups. Alternatively mice were treated by (FIG. 10B) Dexamethasone (DEXA) at 100 μg (□) injected once every 2 days from disease onset; PBS (Δ) or 150 μg pe12-pal (●) injected once every 3 days from disease onset; or 200 μg pe12-pal (▲) injected once every 5 days from disease onset. Values are shown for days 25-35 (mean±SEM). (*) P=0.002, (**) P=0.012, difference between peptide and untreated groups.

FIG. 11A-11D: The peptides reduce symptoms of experimental autoimmune encephalitis (EAE). Graphs showing encephalitic score in mice induced with EAE. Symptoms were observed from day 10 (■) (mean±SEM). Solumedrol at 20 mg/kg (□), PBS (Δ) or peptide was injected from day 1, according to the following regime.

FIG. 11A shows encephalitic score for mice subjected to daily injections of 50 μg p2TB (▲) or 100 μg pe12-pal (●). (*) P≤0.001, difference between peptide and untreated groups.

FIG. 11-B-FIG. 11-D show encephalitic score for mice subjected to daily injections of 50 μg p2TB (●) (FIG. 11B), 10 μg p2TB-pal (●) or 50 μg p2TB-pal (▲) (FIG. 11C) or 100 μg pe12-pal (●) (FIG. 11D). Encephalitic score for mice subjected to injections once every 3 days of 100 μg p2TB (▲)(FIG. 11B), 100 μg p2TB-pal (♦) (FIG. 11C) or 150 μg pe12-pal (▲)(FIG. 11D). Values are shown for days 10-32 (mean±SEM). (*) P≤0.003, () P=0.007, (*) P≤0.015, difference between peptide and untreated groups.

Figure 12A:
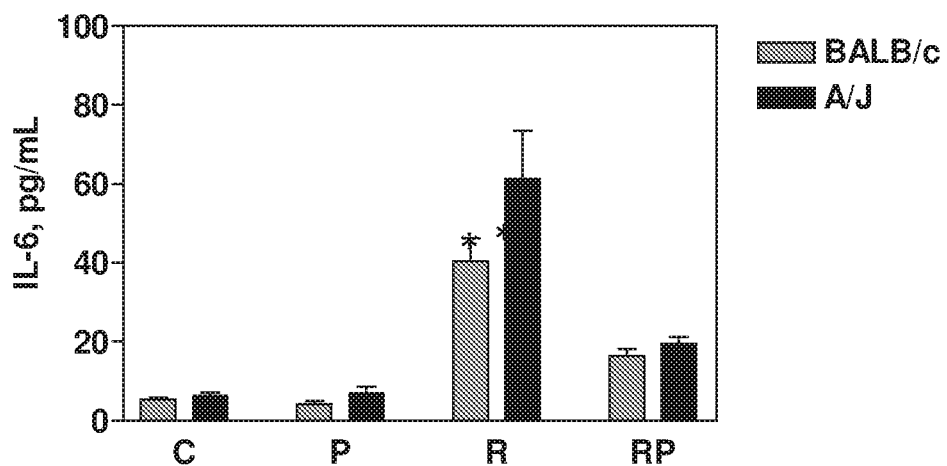
Figure 12B:
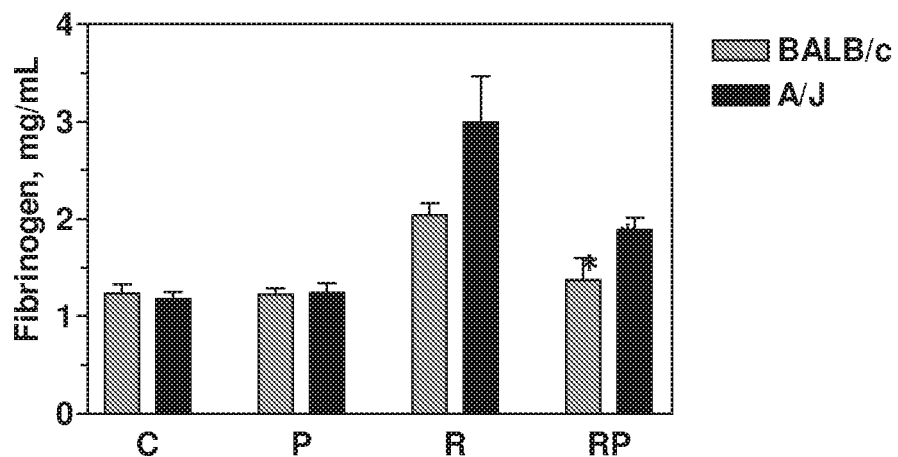

FIG. 12A-12B: Effect of p2TA peptide on systemic inflammatory mediators. Bar graphs of plasma levels of IL-6 (FIG. 12A), or fibrinogen (FIG. 12B) measured in mice on day 7 after irradiation are shown. Abbreviations: C, sham-irradiated mice; P, sham-irradiated mice that received 5 mg/kg of the p(D-Ala)-p2TA-(D-Ala) peptide; R, 8Gy-irradiated mice; and RP, 8Gy-irradiated mice that received 5 mg/kg of the p2TA peptide 24 hours after irradiation. Bars represent the means+SEM of 4-5 mice. An asterisk (*) denotes statistically significant difference between the R and RP groups ($P<0.05$).

Figure 13A:
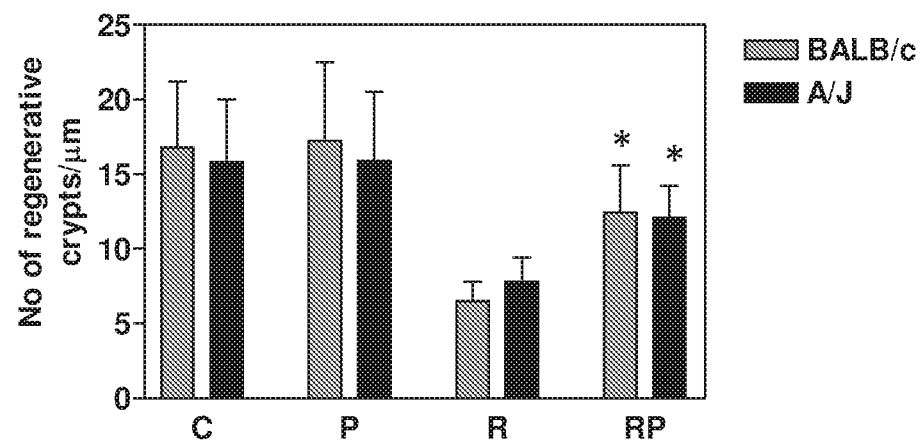
Figure 13B:
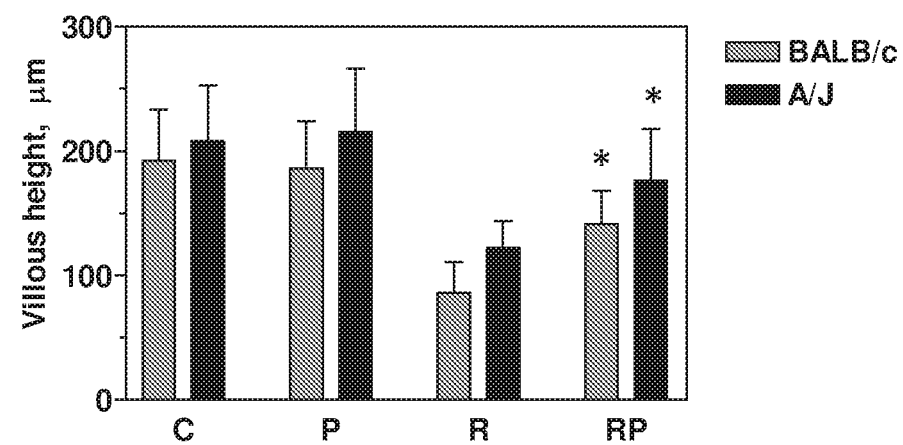
Figures 16A, 16B, 16C, 16D, 16E, 16F, 16G, 16H:
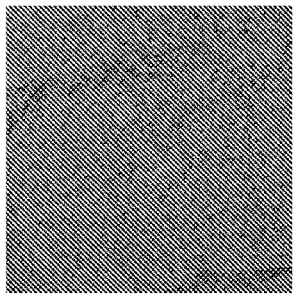

FIG. 13A-13B: Effect of p2TA peptide on jejunal crypts. Bar graphs showing the number of surviving crypts (FIG. 13A) and villous height (FIG. 13B) measured in jejunal tissues that were collected from mice 7 days after irradiation, embedded in paraffin, fixed and processed by staining cross sections with hematoxylin and eosin. Bars represent the means+SEM of 4 cross-sections for each mouse, and 4-5 mice in each group. An asterisk (*) denotes statistically significant difference between R and RP groups ($P<0.05$).

FIG. 14A-14H: The effect of p2TA peptide on Cyclin D1 expression in mouse intestine jejunal crypts. Micrographs showing jejunal tissues that were collected from BALB/c (FIG. 14A-FIG. 14D) and A/J (FIG. 14E-FIG. 14H) mice 7 days after irradiation, embedded in paraffin, fixed and processed by staining cross sections with hematoxylin and eosin. Abbreviations: C, sham-irradiated mice; P, sham-irradiated mice that received 5 mg/kg of (D-Ala)-p2TA-(D-Ala) peptide; R, 8Gy-irradiated mice; RP, 8Gy-irradiated mice that received 5 mg/kg of p2TA peptide 24 hours after irradiation.

FIG. 15A-15H: Immunohistochemistry of jejunum tissue. Cross-sections from jejunum tissues that were immune-stained with COX-2 antibody are shown. Tissues were collected from BALB/c (FIG. 15A-FIG. 15D) and A/J (FIG. 15E-FIG. 15H) mice 7 days after irradiation and embedded in paraffin for immunohistochemistry staining. Abbreviations: C, sham-irradiated mice; P, mice that received 5 mg/kg of the (D-Ala)-p2TA-(D-Ala) peptide; R, 8Gy-irradiated mice; RP: 8Gy-irradiated mice that received 5 mg/kg of the p2TA peptide 24 hours after irradiation.

FIG. 16A-16H: Immunohistochemistry of spleen tissue. Cross-sections from spleen tissue that were immune-stained with COX-2 antibody are shown. Tissues were collected from BALB/c (FIG. 16A-FIG. 16D) and A/J (FIG. 16E-FIG. 16H) mice 7 days after irradiation and embedded in paraffin for immunohistochemistry staining. Abbreviations: C, sham-irradiated mice; P, mice that received 5 mg/kg of the (D-Ala)-p2TA-(D-Ala) peptide; R, 8Gy-irradiated mice; RP: 8Gy-irradiated mice that received 5 mg/kg of the p2TA peptide 24 hours after irradiation.

Figure 17:
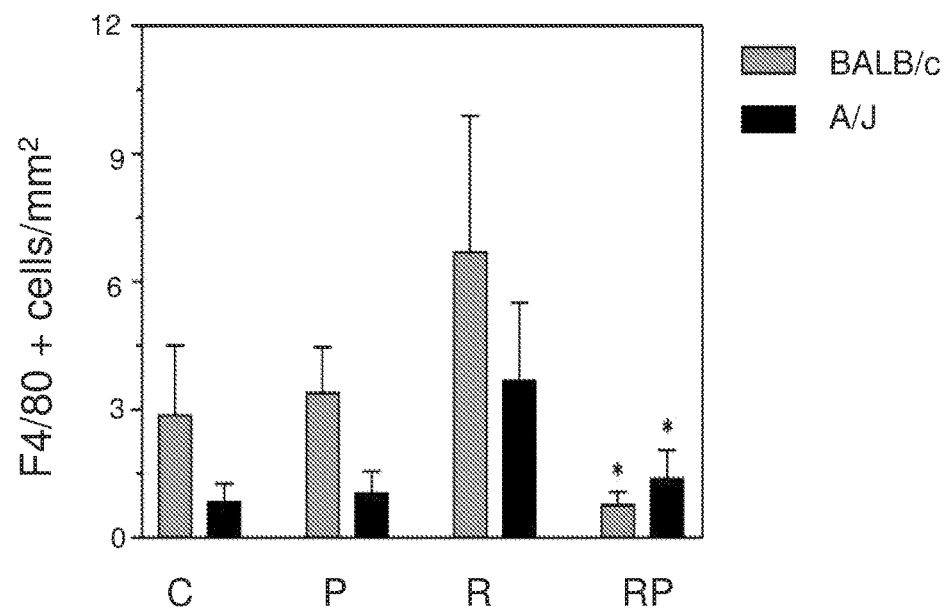

FIG. 17: Immunohistochemistry of activated macrophage marker F4/80 in mouse jejunum. A bar diagram showing the F4/80 positive cells per $mm^2$ in jejunal tissues Abbreviations: C, sham-irradiated mice; P, mice that received 5 mg/kg of the (D-Ala)-p2TA-(D-Ala) peptide; R, 8Gy-irradiated mice; RP: 8Gy-irradiated mice that received 5 mg/kg of the p2TA peptide 24 hours after irradiation. Bars represent the means±SEMs for tissue sections of mice in each group. *Statistically significant differences between R and RP groups ($P<0.05$).

DETAILED DESCRIPTION OF EMBODIMENTS

Figures 4A, 4B, 4C:
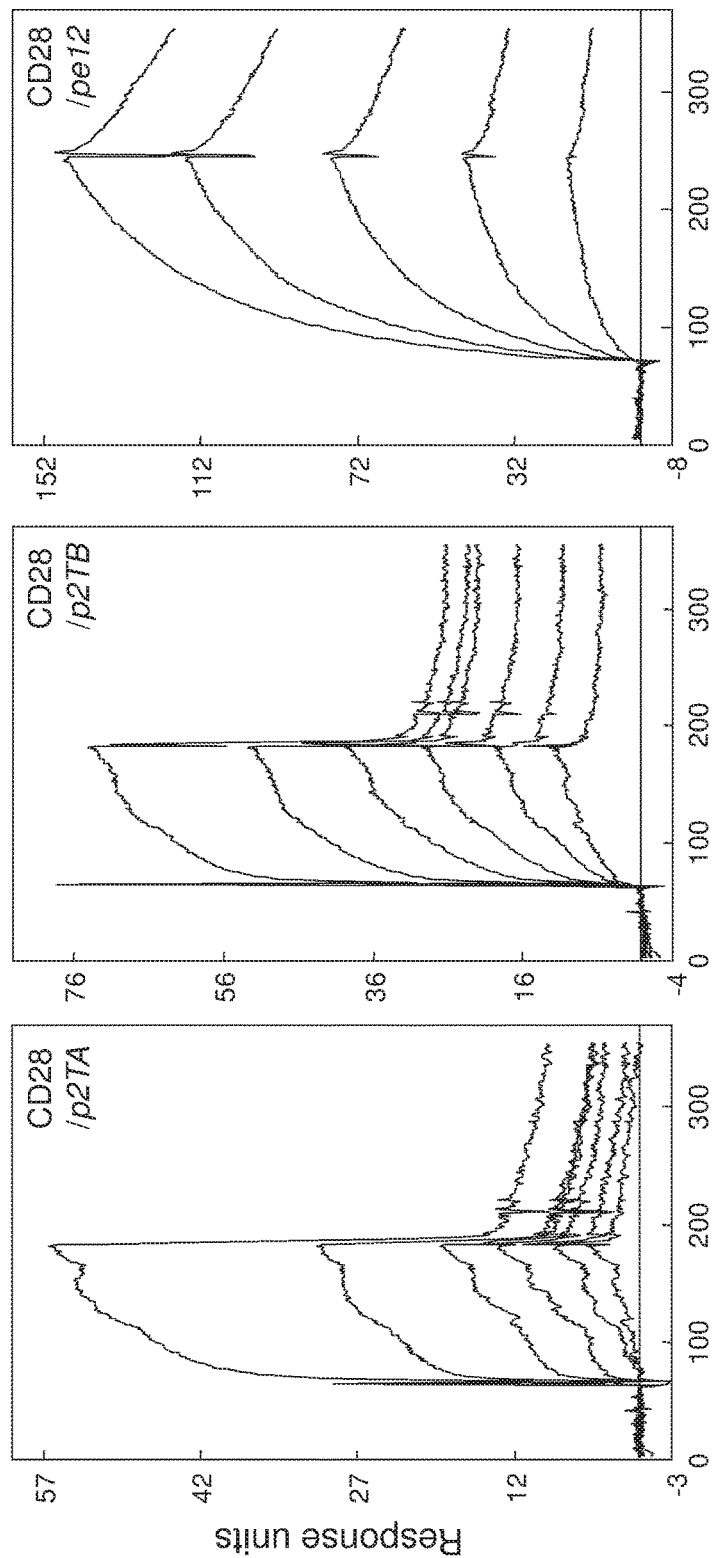
FIG. 4A-4C: Binding of peptides to CD28. Graphs showing representative SPR responses for binding of CD28-Fc to immobilized (D-Ala)-p2TA-(D-Ala) (700 resonance units (rU), FIG. 4A), p2TB (660 rU, FIG. 4B) and pe12 (1,260 rU, FIG. 4C). Analyte concentrations increased in twofold increments from 0.2 μM (FIG. 4A, FIG. 4B) and 0.125 μM (FIG. 4C).

The present disclosure is based on the finding that short peptides, for example about 8 amino acid residues in length, which can specifically bind to the homodimer interface of the costimulatory receptor CD28 with high binding affinity, are capable of inhibiting signaling through CD28 and reduce symptoms of inflammatory disease in various animal models ranging from adjuvant arthritis and collagen-induced arthritis to experimental autoimmune encephalitis. These peptides are generally derived from regions in the amino acid sequence of CD28 that harbor at least one amino acid residue of the residues forming homodimeric contacts (as described, for example, in FIG. 2 of Evans et al. (11)—pale blue coloured residues, and FIG. 4A of Arad et al. 2011 (3), blue coloured residues. The residues forming homodimer contacts are (position in sequence ID NO: 1 is in brackets) Pro at (9), Met at (10), Leu at (41), Val at (86), Thr at (89), Ile at (91), Asn at (111), Gly at (112), Ile at (114) and His at (116) of the amino acid sequence of human CD28 (SEQ ID NO: 1), and define the crystallographic homodimer interface of human CD28. Regions in the human CD28 amino acid sequence from which peptides used in the present invention are derived are, for example, amino acids 10-15 and 116-121 of SEQ ID NO: 1, but also disclosed are peptides not specifically derived from these regions, but which comprise one or more amino acid residues of those amino acid residues which form homodimeric contacts. The terms "crystallographic homodimer interface" and "homodimer interface" may be used herein interchangingly.

Also encompassed by this disclosure and used in the compositions and methods thereof are peptides derived from the crystallographic homodimer interface of human CTLA4. Amino acid residues which form homodimeric contacts as shown (filled circles and blue) in FIG. 2C of Schwartz et al. (12) and also in FIG. 4A of Arad et al 2011 (3). These are amino acid residues at positions 10, 12, 13 and 15 and positions 115-120 of the amino acid sequence of human CTLA4 (SEQ ID NO: 2). Regions in the human CTLA4 amino acid sequence from which peptides used in the present invention are derived are, for example, amino acids 10-15 and 115-120 of SEQ ID NO: 2, generally, peptides which comprise amino acid residues of those residues which form crystallographic homodimer interface in the CTLA4 sequence.

Further encompassed by this disclosure and used in the compositions and methods thereof are peptides selected by phage display for their affinity for the extracellular domain of CD28, which are not homologous or derived to the CD28 sequence or CTLA4 molecule, or regions therein which comprise amino acids of their crystallographic dimer interface as defined above, but rather are different peptides that show a high binding affinity for the crystallographic dimer interface of CD28 and exhibits biological activity in inhibiting non-pathogen induced inflammatory response. These peptides will be described and exemplified in more detailed below.

The above peptides bind directly to CD28, and are effective in reducing disease symptoms in these animal models.

In addition, the present disclosure is based on the surprising effect of the CD28 mimetic peptides, specifically the exemplified p2TA (SEQ ID NO: 47) on radiation-induced inflammatory injuries. This effect was examined in a mouse model subjected to whole-body irradiation, followed by administration of the CD28 mimetic peptide 24 hours post-radiation and evaluation of gastrointestinal tissue damage by analysis of jejunum histopathology and immunohistochemistry for cell proliferation (cyclin D1) and inflammation (COX-2).

Thus, in one of its aspects the present disclosure provides an isolated peptide which specifically binds to the crystallographic homodimer interface of CD28, or a pharmaceutical composition comprising said isolated peptide, for use in a method for the treatment of a non-pathogen associated inflammatory disorder.

The term "peptide" as herein defined refers to a molecular chain of amino acid residues, which, if required, can be modified at each one of its amino acid residues, for example by manosylation, glycosylation, amidation (for example C-terminal amides), carboxylation or phosphorylation. The peptide may be obtained synthetically, through genetic engineering methods, expression in a host cell, or through any other suitable means. Methods for producing peptides are well known in the art.

The term "isolated" refers to molecules, such as amino acid sequences or peptides that are removed from their natural environment, isolated or separated.

The term "amino acid" as used herein, refers to naturally occurring and synthetic amino acid residues, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. The term amino acid also encompasses D-amino acids, which are mirror images of L-amino acids, where the chirality at carbon alpha has been inverted.

The terms "Amino acid sequence" or "peptide sequence" also relate to the order in which amino acid residues, connected by peptide bonds, lie in the chain in peptides and proteins. The sequence is generally reported from the N-terminal end containing free amino group to the C-terminal end containing free carboxyl group.

The term "isolated peptide" as herein defined refers to an isolated peptide, i.e. a peptide of definite length or definite number of consecutive amino acid residues, which is not part of a longer amino acid sequence.

The "peptides for use" in the present disclosure, and their functional derivatives and fragments are isolated peptides which specifically bind to the crystallographic homodimer interface of human CD28. The crystallographic homodimer interface of CD28 is determined by the amino acids Pro at (9), Met at (10), Leu at (41), Val at (86), Thr at (89), Ile at (91), Asn at (111), Gly at (112), Ile at (114) and His at (116) of the amino acid sequence of human CD28 (SEQ ID NO: 1).

Such peptides can be corresponding to a region of from 6 to 14 consecutive amino acid residues within human CD28, which region harbors one or more amino acid residues of the of the crystallographic homodimer interface (as listed above). Examples of such regions within human CD28 are region comprising the amino acid residues 10-15 (peptide p2TA) or 116-121 (peptide p1TA) of SEQ ID NO: 1. Other peptides used in the present disclosure, exemplified below, are derived from other such region in human CD28 (SEQ ID NO: 1) such as p3TA, p4TA and p5TA (3). Other peptides used in the methods and composition of the present disclosure are isolated peptides which specifically bind to the crystallographic homodimer interface of human CD28 and correspond to a region within human CTLA4 (SEQ ID NO: 2) of from 6 to 14 consecutive amino acid residues within human CTLA4, which region harbors one or more amino acid residues of the of the crystallographic homodimer interface of CTLA4. (as listed below). Examples of such regions are amino acid residues 10-15 (peptide p2TB) or 115-120 (peptide p1 TB) of SEQ ID NO: 2. Still further, peptides for use in the methods and compositions disclosed herein are various peptides that do not necessarily have homology to human CD28 or human CTLA4, but do bind to the crystallographic homodimer interface of human CD28 with high affinity, and inhibit non-pathogen induced inflammatory response.

By the terms "corresponding to" or "derived from" a reference amino acid sequence as used herein is meant that the corresponding/derived amino acid is essentially identical to the reference amino acid sequence, but can include variations, as herein defined for "derivatives" and "fragments".

Direct evidence is presented in the appended examples that the isolated peptides for use in accordance with the present disclosure inhibit signaling for inflammatory cytokine production in human PBMC when it is transduced via CD28 (FIG. 2) and moreover, that each peptide is capable of binding directly to CD28, with an affinity estimated to be in the micromolar range (FIG. 4).

Thus in some embodiments the isolated peptides for use according to the present invention have a binding affinity to the homodimer interface of human CD28 that is characterized by a $K_D$ lower than 30 micromolar, more specifically $K_D$ of from about 0.1 to about 30 micromolar. For example, $K_D$ of (D-Ala)-p2TA-(D-Ala) binding is 2 micromolar.

Thus, the isolated peptide for use as herein defined is characterized by at least one of (i) specific binding to the crystallographic homodimer interface of human CD28 with a $K_D$ lower than 30 micromolar, more specifically $K_D$ of from about 0.1 to about 30 micromolar, and (ii) being able to inhibit non-pathogen induced inflammatory response as determined by a reduction in the level of at least one of the inflammatory cytokines IL2, interferon-γ (IFN-γ) and tumor necrosis factor-α (TNF-α) and/or by reduction in the level of cyclooxygenase 2 (cox-2) and/or by a decrease in the number of F4/80-positive cells. Other biological parameters indicating severity of inflammation may be used. The binding affinity of the peptides used in the present invention for the CD28 homodimer interface is thus characterized by $K_D$ lower than 30 micromolar, more specifically $K_D$ of from about 0.1 to about 30 micromolar, for example $K_D$ of from about 0.1, 0.2, 0.3, 04, 0.5, 1.0, 2.0, 3.0, 4.0, 5.0, 10, 15, 20 or 25 to about 30 micromolar.

In some embodiments the isolated peptide for use according to the invention is a functional fragment or derivative of said the above defined peptides, which functional fragments or derivatives maintain the ability to bind to said homodimer interface of human CD28 at a binding affinity lower than 30 micromolar.

Alignment of human and mouse CD28 shows that within the p2TA domain [amino acid residues 8-15 of SEQ ID NO: 1] there is extensive sequence variation, with 4 out of 8 amino acids differing (SPMLVAYD vs. SPLLVVDS), yet the human peptide reduced symptoms of pathology in different rodent models of arthritis. The hydrophobic nature of this domain (5 out of 8 amino acids) is conserved between human and mouse CD28. This may satisfy the requirement of the peptide to engage the site recognized by the p2TA domain within the CD28 homodimer. Apparently, it is not the specific peptide sequence that imparts the ability to interact with CD28, reducing signaling through this receptor and protecting from disease, but the overall nature of the peptide in which hydrophobic residues are dominant. pe12 (SEQ ID NO: 49), as expected from its selection by phage display, and p2TB (SEQ ID NO: 48) each bound the extracellular domain of CD28 and reduced CD28 signaling. If the human p2TA peptide matches the dimer interface in mouse CD28 despite sequence extensive variation, then the similarly hydrophobic sequence of p2TB (SEQ ID NO: 9) may account for its interaction with CD28, be it human (FIG. 2B) or murine.

In some non-limiting embodiments, the isolated peptide which specifically binds to the homodimer interface of CD28 according to the invention is (i) derived from a region in human CD28 that comprises amino acid residues forming homodimeric contacts, for example from the sequence of amino acid residues 10-15 or 116-121 of SEQ ID NO: 1 or (ii) derived from a region in human CTLA4 that comprises amino acid residues forming homodimeric contacts, for example amino acid residues 10-15 or 115-120 of SEQ ID NO: 2.

An N-terminal palmitoyl tail was added to the peptides, speculating that anchoring them through a hydrophobic tail into the cell membrane might enhance their ability to interact with CD28. However, this modification did not enhance efficacy of p2TB in Collagen Induced Arthritis (CIA) or Experimental Autoimmune encephalitis (EAE). Whether or not it was modified, each of the peptides examined had a significant effect in reducing symptoms of inflammatory disease. The inventors thus concluded that it is not the palmitoyl tail but the amino acid sequence itself that renders the peptide effective.

In further embodiments the isolated peptide which specifically binds to the homodimer interface of human CD28 according to the invention is:

(a) (i) a peptide derived from human CD28, consisting of the amino acid sequence HVKGKHLCP as denoted by SEQ ID NO: 3, also termed herein p1TA or consisting of the amino acid sequence SPMLVAYD as denoted by SEQ ID NO: 4, also termed herein p2TA or consisting of the amino acid sequence HKGLDSAV (SEQ ID NO: 5) also termed herein p3TA, or consisting of the amino acid sequence YVNQTDIY (SEQ ID NO: 6), also termed herein p4TA, or consisting of the amino acid sequence NGTIIHVKG (SEQ ID NO: 7), also termed herein p5TA;

(ii) a peptide derived from human CTLA4 consisting of the amino acid sequence YVIDPEPCP as denoted by SEQ ID NO: 8, also termed herein p1TB or the amino acid sequence PAVVLASS as denoted by SEQ ID NO: 9, also termed p2TB;

(iii) a peptide selected from the group consisting of a p12A (as denoted by SEQ ID NO: p12B (as denoted by SEQ ID NO: 11), pe12 (SEQ ID NO: 12), or pe12-D-Ala (as denoted by SEQ ID NO: 49) or pal-pe12-(D-Ala) (as denoted by SEQ ID NO: 51), pd7 (as denoted by SEQ ID NO: 13) and pc3 (as denoted by SEQ ID NO: 14); pa2 (as denoted by SEQ ID NO: 15), pb4 (as denoted by SEQ ID NO: 16), pc11 (as denoted by SEQ ID NO: 17), pf11 (as denoted by SEQ ID NO: 18), pg3 (as denoted by SEQ ID NO: 19), pb12 (as denoted by SEQ ID NO: 20), pa8.1 (as denoted by SEQ ID NO: 21), pb3 (as denoted by SEQ ID NO: 22), pb5 (as denoted by SEQ ID NO: 23), pc5 (as denoted by SEQ ID NO: 24), pf3 (as denoted by SEQ ID NO: 25), pf8 (as denoted by SEQ ID NO: 26), pe6 (as denoted by SEQ ID NO: 27), pf4 (as denoted by SEQ ID NO: 28), pa8.2 (as denoted by SEQ ID NO: 29), b7 (as denoted by SEQ ID NO: 30), pb2 (as denoted by SEQ ID NO: 31), pc2 (as denoted by SEQ ID NO: 32), pc8 (as denoted by SEQ ID NO: 33), pc9 (as denoted by SEQ ID NO: 34), pf12 (as denoted by SEQ ID NO: 35), pc4 (as denoted by SEQ ID NO: 36), pe11 (as denoted by SEQ ID NO: 37), pb5 (as denoted by SEQ ID NO: 38), pe13 (as denoted by SEQ ID NO: 39), pg7 (as denoted by SEQ ID NO: 40), pa12 (as denoted by SEQ ID NO: 41), pb8 (as denoted by SEQ ID NO: 42), pb12 (as denoted by SEQ ID NO: 43), pc8 (as denoted by SEQ ID NO: 44), pd8 (as denoted by SEQ ID NO: 45), pg6 (as denoted by SEQ ID NO: 46);

(b) peptides which are at least 80% homologous to the above (a), wherein the resultant peptide of (b) maintains the ability to specifically bind to said human CD28 homodimer interface, at a binding characterized by a $K_D$ lower than 30 micromolar, more specifically $K_D$ of from about 0.1 to about 30 micromolar, and inhibit a non-pathogen induced inflammatory response as determined by at least one of the inflammatory cytokines IL2, interferon-γ (IFN-γ) and tumor necrosis factor-α (TNF-α) and/or by reduction in the level of cyclooxygenase 2 (cox-2) and/or by a decrease in the number of F4/80-positive cells;

(c) a peptide of (a) or (b) that is extended at the N terminus and/or the C terminus:
   (i) by a lauryl cysteine at the N terminus and a cysteine at the C terminus; or
   (ii) by an organic moiety that is not a naturally occurring or synthetic amino acid residue; or
   (iii) by identical hydrophobic amino acid residue(s) which may be naturally occurring or synthetic amino acid residues; or
   (iv) by a palmitoyl-lysine tail, wherein said tail is at the N terminus, wherein the resultant peptide of (c) maintains the ability to specifically bind to the said human CD28 homodimer interface and inhibit an inflammatory response as determined by at least one of the inflammatory cytokines IL2, interferon-γ (IFN-γ) and tumor necrosis factor-α (TNF-α) and/or by reduction in the level of cyclooxygenase 2 (cox-2) and/or by a decrease in the number of F4/80-positive cells; or
(d) a dimer or multimer of (a), (b) or (c), wherein the resultant peptide of (d) maintains the ability to specifically bind to the said human CD28 homodimer interface at a binding affinity characterized by $K_D$ of lower than 30 micromolar, more specifically $K_D$ of from about 0.1 to about 30 micromolar, and inhibit an inflammatory response as determined by at least one of the inflammatory cytokines IL2, interferon-γ (IFN-γ) and tumor necrosis factor-α (TNF-α) and/or by reduction in the level of cyclooxygenase 2 (cox-2) and/or by a decrease in the number of F4/80-positive cells.

Fragments or derivatives of the isolated peptides as herein defined are also encompassed by the present invention. The terms fragments or derivatives are meant to include peptides which differ in one or more amino acids in the overall sequence, namely, which have deletions, substitutions (e.g. replacement of at least one amino acid by another amino acid by conservative substitution), inversions or additions. This term also encompasses the replacement of at least one amino acid residue in the overall sequence by its respective D amino acid residue.

Amino acid "substitutions" are the result of replacing one amino acid with another amino acid having similar structural and/or chemical properties, i.e., conservative amino acid replacements Amino acid substitutions may be made on the basis of similarity in polarity, charge, solubility, hydrophobicity, hydrophilicity, and/or the amphipathic nature of the residues involved. For example, each of the following eight groups contains amino acids that are conservative substitutions for one another:
  1) Alanine (A), Glycine (G);
  2) Aspartic acid (D), Glutamic acid (E);
  3) Asparagine (N), Glutamine (Q);
  4) Arginine (R), Lysine (K);
  5) Isoleucine (I), Leucine (L), Methionine (M), Valine (V);
  6) Phenylalanine (F), Tyrosine (Y), Tryptophan (W);
  7) Serine (S), Threonine (T); and
  8) Cysteine (C), Methionine (M).

Fragments of the peptide as herein defined are also included in the present invention. The term "fragment" refers to any peptide which is at least one amino acid shorter than the isolated peptide in accordance with the invention, obtained by deletion of at least one amino acid residue from the peptide in accordance with the invention.

In some embodiments the peptides can be coupled through their N-terminus to a lauryl-cysteine (LC) residue and/or through their C-terminus to a cysteine (C) residue, or to other residue/s suitable for linking the peptide to adjuvant/s for immunization.

The peptides of the present disclosure may all be positively charged, negatively charged or neutral. In addition, they may be in the form of a dimer, a multimer or in a constrained conformation, which can be attained by internal bridges, short-range cyclizations, extension or other chemical modifications.

Further, the peptides may be extended at the N-terminus and/or C-terminus thereof with various identical or different amino acid residues. As an example for such extension, the peptide may be extended at the N-terminus and/or C-terminus thereof with identical or different hydrophobic amino acid residue/s which may be naturally occurring or synthetic amino acid residue/s. A preferred synthetic amino acid residue is D-alanine. An additional example for such an extension may be provided by peptides extended both at the N-terminus and/or C-terminus thereof with a cysteine residue. Naturally, such an extension may lead to a constrained conformation due to Cys-Cys cyclization resulting from the formation of a disulfide bond. Another example may be the incorporation of an N-terminal palmitoyl-lysine tail, the lysine serving as linker and the palmitic acid as a hydrophobic anchor. In addition, the peptides may be extended by aromatic amino acid residue/s, which may be naturally occurring or synthetic amino acid residue/s, for example a specific aromatic amino acid residue may be tryptophan. The peptides may be extended at the N-terminus and/or C-terminus thereof with one or more amino acids present in corresponding adjacent positions of the amino acid sequence of the naturally occurring human CD28 or human CTLA4, for example one, two or three consecutive amino acid residues of the naturally occurring sequence. The peptides may be extended at the N-terminus and/or C-terminus thereof with various identical or different organic moieties which are not a naturally occurring or synthetic amino acids. As an example for such extension, the peptide may be extended at the N-terminus and/or C-terminus thereof with an N-acetyl group. For every single peptide sequence used by the invention and disclosed herein, this invention includes the corresponding retro-inverse sequence wherein the direction of the peptide chain has been inverted and wherein all the amino acids belong to the D-series. Longer peptides in which the basic epitope sequence which comprises part or all of the amino acid sequence of said peptide/s, or in which the basic peptidic sequence of any one of these peptides is repeated from about 2 to about 100 times are also contemplated.

It is appreciated that these peptide fragments or derivatives must not alter the biological activity of the original peptide. The terms "functional" or "without significantly affecting the biological characteristics of the modified peptide as compared to the unmodified peptide" means to denote that the modified peptide retains a biological activity qualitatively similar to that of the unmodified peptide.

The term "biological activity characteristics" when referring to the isolated peptides of the invention encompasses peptides that inhibit an inflammatory response as determined by at least one of the inflammatory cytokines IL2, interferon-γ (IFN-γ) and tumor necrosis factor-α (TNF-α) and/or by reduction in the level of cyclooxygenase 2 (cox-2) and/or by a decrease in the number of F4/80-positive cells, and any other suitable parameters.

Thus, in order to determine whether a peptide derivative or fragment qualitatively and quantitatively retains biological characteristics similar to that of the unmodified peptide, one or more assays can be carried out, such as for example the determination of at least one of the inflammatory cytokines IL2, interferon-γ (IFN-γ) and tumor necrosis factor-a (TNF-α) and/or of reduction in the level of cyclooxygenase 2 (cox-2) and/or of the decrease in the number of F4/80-positive cells, for example, in the manner described in the Examples below.

In a specific embodiment, the isolated peptide consists of the amino acid sequence SPMLVAYD denoted by SEQ ID NO. 4 (peptide p2TA) or the amino acid sequence (D-A) SPMLVAYD(D-A) denoted by SEQ ID NO. 47 (peptide (D-A)-p2TA-(D-A). As specified below, the name p2TA (as well as all other arbitrary peptide names) can sometimes be used herein to designate both the core sequence (SEQ ID NO. 4) or its D-Ala abutted derivative (ID NO. 47).

Other specific peptides are a peptide consisting of the amino acid sequence as denoted by SEQ ID NO: 5, designated p3TA, a peptide consisting of the amino acid sequence as denoted by SEQ ID NO: 6, designated p4TA, and a peptide consisting of the amino acid sequence as denoted by SEQ ID NO: 7, designated p5TA. These peptides exhibit biological activity similar to that of p2TA (Arad 2011, (3)). The D-Ala derivatives and palmitoyl-lysine derivatives are also encompassed hereby.

In another embodiment, the isolated peptide consists of the amino acid sequence PAVVLASS (denoted by SEQ ID NO: 9, peptide p2TB), (D-A)PAVVLASS(D-A) (denoted by SEQ ID NO: 48, peptide (D-A)-p2TB-(D-A) and (palmitoyl-lysine)PAVVLASS(D-A) (denoted by SEQ ID NO: 50, (pal)-p2TB-(D-A)).

In another embodiment, the isolated consists of the amino acid sequence SHFTHNRHGHST (denoted by SEQ ID NO: 12, peptide pe12), (D-A)SHFTHNRHGHST(D-A) (denoted by SEQ ID NO: 49, peptide pe12-(D-A)) and (palmitoyl-lysine)SHFTHNRHGHST(D-A) (denoted by SEQ ID NO: 51, peptide pe12-pal).

As indicated above, the present disclosure is based on the finding that short peptides, for example of about 8 amino acid residues in length (e.g. the peptide termed herein p2TA), which can specifically bind to the crystallographic homodimer interface of the costimulatory receptor CD28 with high binding affinity, are capable of inhibiting signaling through CD28 and thereby reduce symptoms of inflammatory disease in various animal models ranging from adjuvant arthritis and collagen-induced arthritis to experimental autoimmune encephalitis (as detailed in Examples 4-6).

In addition, the results presented below suggest that modulation of the immune system responses following total body IR exposure by the p2TA peptide acts as a potent mitigator of IR damage.

The common feature of all of these inflammatory disorders or diseases is the fact that they are not associated with an invading pathogen, namely they can be defined as "non-pathogen associated inflammatory disorders". The terms "non-pathogen associated inflammatory disorders", "non pathogen induced inflammatory disorders", "non-pathogen related inflammatory disorders" may be used herein interchangingly.

Therefore, as indicated above, the present disclosure provides an isolated peptide which specifically binds to the crystallographic homodimer interface of CD28, or a pharmaceutical composition comprising said isolated peptide, for use in a method for the treatment of a non-pathogen associated inflammatory disorder.

The terms "treat", or forms thereof, and the terms "alleviating" and "mitigating" mean to at least partially ameliorate or cure the patient's disease or condition as defined herein. The "treat" as used herein is also to be taken to mean adding supportive therapy to the treatment by the peptide disclosed herein. For example, in case of radiation induced inflammation, radiation supportive therapy may be added.

Thus the term "non pathogen associated inflammatory disorder" as herein defined refers to an inflammatory disease, disorder or condition that is not associated with a pathogen. Pathogens can be any one of bacterial toxins, bacteria, viruses, fungi, worms, plants and other living organisms capable of infecting humans. Specific such pathogens may be Gram-positive bacteria, Gram-negative bacteria, mixtures thereof leading to polymicrobial infection, bacterial toxins and other toxic bacterial components such as exotoxins, endotoxins, superantigen toxins, pathogen associated molecular patterns (PAMPs), Damage Associated Molecular Pattern molecules (DAMPs), lipopolysaccharides, peptidoglycans or toxic components thereof, molecules that are associated with groups of pathogens that are recognized by cells of the innate immune system and molecules that are associated with groups of pathogens that are recognized by Toll-like receptors (TLRs).

In some embodiments the inflammatory disorder is any one of radiation-induced inflammation, inflammatory bowel disease (IBD), radiation-induced gastroenteritis, drug-induced inflammation, arthritis, rheumatoid arthritis, osteoarthritis, lupus, myasthenia gravis, multiple sclerosis, adult respiratory distress syndrome (ARDS), asthma, rhinitis, idiopathic pulmonary fibrosis, peritonitis, cardiovascular inflammation, myocardial ischemia, reperfusion injury, atherosclerosis, trauma, diabetes type II, retinopathy, psoriasis, gastrointestinal inflammation, cirrhosis, appendicitis, bursitis, colitis, cystitis, dermatitis, phlebitis, vasculitis, acne vulgaris, and pelvic inflammatory disease.

In some embodiments the inflammatory disease or condition is radiation-induced inflammation.

The term "radiation-induced inflammation" as herein defined refers to inflammation associated or resulting from radiation therapy. It has been reported that effects of ionizing radiation, characteristically associated with the consequences of energy deposition in the cell nucleus, arise at the site of the irradiated cells as well as in non-irradiated cells, consistent with a known delayed and long-lived tissue reaction to radiation injury characteristic of an inflammatory response with the potential for persisting damage. An important implication of these findings is that contrary to conventional radiobiological dogma and interpretation of epidemiologically-based risk estimates, ionizing radiation may contribute to further malignancy.

As detailed below, the levels of the pro-inflammatory cytokine IL-6 increased significantly in mouse plasma 7 days after radiation exposure. Surprisingly, administration of the p2TA peptide significantly reduced the elevation of IL-6 and the radiation-induced production of fibrinogen. In addition, the examples below demonstrate that the irradiated R group had significantly fewer intestinal crypt cells and shorter villi compared to the control C group. Overall, the p2TA peptide had a protective effect on radiation-induced intestinal injury, inducing improved morphology of villi and crypts, increased cyclin D1 expression and decreased COX-2 staining. These observations suggest that attenuation of CD28 signaling is a promising therapeutic approach for mitigation of radiation-induced tissue injury.

As defined herein, the term "radiation" or "ionizing radiation" refers to radiation therapy (or "radiotherapy"), which is the medical use of ionizing radiation, generally as part of cancer treatment to control or kill malignant cells. Radiation therapy may be used as palliative treatment or as therapeutic treatment. Most common cancer types can be treated with radiation therapy in some way, and various types of radiation treatments are used. For example, "total body irradiation" (TBI) is a radiation therapy technique used to prepare the body to receive a bone marrow transplant.

Radiation therapy has also several applications in non-malignant (non-cancerous) conditions, such as the treatment of trigeminal neuralgia, acoustic neuromas, severe thyroid eye disease, pterygium, pigmented villonodular synovitis, and prevention of keloid scar growth, vascular restenosis, and heterotopic ossification. The use of radiation therapy in non-malignant conditions is limited partly by worries about the risk of radiation-induced cancers.

As indicated above, radiation therapy may be used in the treatment of a variety of disorders. Special care is taken by radiation oncologists to minimize exposure to radiation. Nonetheless, radiation therapy may cause injury to the body at the site of irradiation as well as at remote sites even at low levels. For example, symptoms of radiation injury to the colon and rectum include acute inflammation, decreased mucus production, and accumulation of fluid beneath the intestinal lining.

This disclosure demonstrates that the CD28-mimetic peptide p2TA mitigates many of the effects of ionizing radiation in vivo, both in the systemic circulation and in several tissues including the gastrointestinal (GI) tract. It is known that radiation-induced inflammation of the GI tract is considered to be one of the critical causes for systemic complications following radiation exposure, and may mediate some effects that lead to multiple organ failure.

For example, exposure to high doses of ionizing irradiation causes the loss of cells in jejunal crypts. It has been reported that apoptosis levels in crypt cells increase dramatically at 3 to 6 hours after exposure to as little as 1 Gy of gamma-rays; where an 8 Gy exposure leads to prolonged apoptosis observed as late as 60 hours following exposure, although its peak occurs at earlier time points. In addition to crypt stem cells, apoptosis of endothelial cells from the GI microvasculature is also considered critical for radiation caused GI toxicity.

Thus in some embodiments the radiation-induced inflammation is systemic and/or at the irradiated site.

In other words, the radiation-induced inflammation encompassed by the present invention may be systemic, namely may affect all the body and/or at the irradiated site, namely at the specific location of radiation.

Therefore by another one of its aspect the present disclosure provides an isolated peptide which specifically binds to the crystallographic homodimer interface of CD28 and functional derivative thereof, or a pharmaceutical composition comprising the same, for use in a method for the treatment of a non-pathogen associated inflammatory disorder. The said isolated peptide and its functional derivatives have a binding affinity for the crystallographic homodimer interface of CD28 characterized by a $K_D$ lower than 30 micromolar, more specifically $K_D$ of from about 0.1 to about 30 micromolar.

The said isolated peptide can have an amino acid sequence derived from a region of human CD28 harboring one or more amino acid residues forming homodimeric contacts or from a region of CTLA4 harboring one or more amino acid residues forming homodimeric contacts, and any functional fragments and derivatives of said peptide, wherein said functional fragments or derivatives maintain the ability to bind to said crystallographic homodimer interface of CD28 at a binding affinity characterized by a $K_D$ lower than 30 micromolar, more specifically $K_D$ of from about 0.1 to about 30 micromolar. The amino acid residues in human CD28 and CTLA4 forming homodimeric contacts are listed above.

In specific embodiments the present disclosure provides an isolated peptide which comprises the amino acid sequence SPMLVAYD denoted by SEQ ID NO: 4 (peptide p2TA) or the amino acid sequence (D-A)SPMLVAYD(D-A) denoted by SEQ ID NO: 47 (peptide (D-A)-p2TA-(D-A)), for use in a method for the treatment of radiation-induced inflammation.

In other embodiments the radiation-induced inflammation is associated with at least one of gastrointestinal tract and spleen inflammation.

Gastrointestinal toxicity can occur following irradiation of thoracic, abdominal, or pelvic malignancies whenever normal gastrointestinal structures are located within the radiation therapy (RT) field Importantly, these toxicities can limit the maximum dose of RT and chemotherapy, and thus may limit the efficacy of treatment. The gastrointestinal side effects of RT include early (acute) toxicity, such as diarrhea and nausea that are experienced during or shortly after the completion of a course of therapy. In addition, late effects may be observed months to years after RT. These late reactions include ulceration, stricture formation, and bowel obstruction.

In further embodiments the inflammatory disorder is radiation-induced gastroenteritis.

The term "radiation-induced gastroenteritis" or "radiation enteritis" as herein defined refers to swelling and inflammation of the lining of the small intestine induced by radiation therapy applied in cancer treatments. Radiation enteritis is usually more severe in patients suffering from diabetes, atherosclerosis, or a history for prior abdominal surgery. The symptoms of radiation enteritis include, but are not limited to, anorexia, diarrhea, nausea, vomiting and weight loss.

By another one of its aspects the present disclosure provides an isolated peptide which specifically binds to the crystallographic homodimer interface of human CD28, or a pharmaceutical composition comprising said isolated peptide, for use in a method of reducing radiation-induced thrombotic risk.

Radiation-induced inflammation may be detected and monitored using any marker and methods known in the art, for example as exemplified herein, namely by tissue analysis for cell proliferation (cyclin D1) and inflammation (COX-2) markers as well as by monitoring the morphology of the irradiated tissue (e.g. monitoring the morphology of villi and crypts in an irradiated intestinal tissue). In addition, specific plasma markers of inflammation may be used, for example, but not limited to the cytokines interleukin 6 (IL-6), tumor necrosis factor, interferon-gamma, IL-1, and fibrinogen.

As exemplified below, the peptide (D-Ala)-p2TA-(D-Ala) (SEQ ID NO: 47) was given to irradiated mice 24 hours after being exposed to IR in order to investigate which of the features associated with IR exposure may be modulated in its presence Importantly, at this time point, for example, apoptosis of crypt stem cells has already reached its peak.

As shown below, in response to treatment with the peptide p2TA, statistically significant differences in the quantity of IL-6 and fibrinogen were noted, as well as a significant decrease in jejunal crypt toxicity induced by IR. In addition, a decrease in COX-2 expression was found in all three tissues tested and an increase in Cyclin D1 was observed in crypt cells.

Without wishing to be bound by theory, it should be noted that Cyclin D1 expressing-crypt cells produce anti-inflammatory glucocorticoids, which may lead to the development of a GI protective anti-inflammatory feedback loop.

To date, many different agents have been used to modulate the in vivo effects of systemic or GI radiation injury, including a variety of cytokines and growth factors, some stimulating growth of intestinal stem cells, others endothelial cells of the microvasculature. Inhibition of COX2 was also suggested as a possible modulator of radiation responses. More recent work examined effects of genistein nanoparticles as radiation mitigators Importantly, however, in each case the proposed mitigating substance was administered either before or shortly after irradiation, or, alternatively, as a continuous, days long post-irradiation treatment. The present disclosure demonstrates that administration of the mitigator was done only once (namely, by a single administration) and as long as 24 hours after exposure to irradiation.

Therefore in some embodiments the isolated peptide or any functional derivatives or fragments thereof or a pharmaceutical composition comprising said isolated peptide as herein defined is administered to said subject at any suitable time prior to and/or post irradiation.

In some specific embodiments the isolated peptide or pharmaceutical composition for use according to the present disclosure is for administration to said subject in need thereof immediately following, or within from about 30 minutes up to any time at which the radiation-induced inflammation persists, whether while the subject is still undergoing radiation therapy, in between radiation therapy treatments or thereafter.

In further specific embodiments the isolated peptide or pharmaceutical composition for use according to the present disclosure is for administration to a subject in need thereof from about 30 minutes to about 60 or 90 minutes, 2, 4, 6, 8, 10, 12, 14, 16, 18, 20, 22, 24, 36, 48, 60 or 72 hours, 4, 5, 6, 7, 14, 32 or 28 days following exposure to said radiation.

In still further embodiments the isolated peptide or pharmaceutical composition for use according to the invention is for administration to said subject within about 24 hours following exposure to said radiation.

As indicated above, the present disclosure is based on the finding that short peptides, for example p2TA, are capable of reducing the symptoms of inflammatory disease in various animal models ranging from adjuvant arthritis and collagen-induced arthritis to experimental autoimmune encephalitis (as detailed in Examples 4-6).

Thus in some embodiments the inflammatory disorder as herein defined is any one of rheumatoid arthritis, multiple sclerosis and myasthenia gravis as well as inflammatory bowel disease (IBD)

The term "rheumatoid arthritis" (RA) as herein defined refers to a chronic, systemic inflammatory disorder that primarily affects joints. It may result in deformed and painful joints, which can lead to loss of function. The disease may also have signs and symptoms in organs other than joints.

The term "multiple sclerosis" also known as disseminated sclerosis or encephalomyelitis disseminata as herein defined refers to an inflammatory disease in which the insulating covers of nerve cells in the brain and spinal cord are damaged. This damage disrupts the ability of parts of the nervous system to communicate, resulting in a wide range of signs and symptoms, including physical, mental, and psychiatric.

The term "myasthenia gravis" as herein defined refers to either autoimmune or congenital neuromuscular disease that leads to fluctuating muscle weakness and fatigue. In the most common cases, muscle weakness is caused by circulating antibodies that block acetylcholine receptors at the postsynaptic neuromuscular junction, inhibiting the excitatory effects of the neurotransmitter acetylcholine on nicotinic receptors at neuromuscular junctions.

In some specific embodiments the inflammatory disorder is drug-induced inflammation.

In further specific embodiments the drug-induced inflammation is any one of drug-induced hepatitis, drug-induced ocular inflammation, drug-induced gastrointestinal damage, drug-induced acute ulcers, drug-induced renal failure, drug-induced pancreatitis, drug-induced nephritis, chemotherapy-induced inflammation in the gastrointestinal tract and seborrheic keratosis.

The isolated peptide or any functional derivatives or fragments thereof or a pharmaceutical composition comprising said isolated peptide as herein defined may be administered in any route of administration.

In some embodiments the isolated peptide or any functional derivatives or fragments thereof or the pharmaceutical composition is administered by a route selected from the group consisting of intravenous, intramuscular or intraperitoneal administration, intrathecal or subcutaneous injection, oral, intrarectal, intranasal ocular and topical administration.

Calculating the "therapeutically effective amount" of the isolated peptide or any functional derivatives or fragments thereof for purposes herein defined is determined by such considerations as are known in the art in order to inhibit, arrest or alleviate inflammation and possibly other side effects induced by or resulting from exposure to ionized radiation.

For example, as exemplified below, irradiated mice were injected with the p2TA peptide by a single administration of 5 mg/kg, with a human equivalent dose of 0.4 mg/kg.

Thus in some specific embodiments the isolated peptide or any functional derivatives or fragments thereof or pharmaceutical composition for use as herein defined is wherein said isolated peptide is administered at an amount of from about 0.05 mg to about 5.0 mg peptide/kg body weight of a subject in need thereof, for example 0.05, 0.1, 0.15, 0.2, 0.25, 0.3, 0.4, 0.5, 1.0, 2.0, 3.0, 4.0 or 5.0 mg peptide/kg body weight of the subject.

The term "subject in need thereof" as used herein means warm-blooded animals, such as for example rats, mice, dogs, cats, guinea pigs, primates and humans suffering from a non-pathogen associated inflammatory disorder as herein defined. The term subject in need thereof also relates to subjects prior to and/or after being exposed to at least one dose of ionizing radiation. The subject in need thereof as herein defined also encompasses any subject already suffering from radiation-induced side effects, in order to improve the quality of life of the subject.

Despite the fact that short peptides have a short half-life in the circulation and they disappear within minutes, they exhibited long-term efficacy, as demonstrated in the appended examples. This remarkable result is supported by the finding that in the adjuvant arthritis model in rats, symptoms did not rebound and even continued to decline over a two-week period after daily treatment with the peptide was terminated, whereas termination of a steroid treatment resulted in a prompt rebound to maximal clinical score.

Moreover, when the long-term efficacy was examined for two of the peptides, reduced disease symptoms were obtained in Collagen-induced arthritis (CIA) and Experimental autoimmune encephalitis (EAE) when administered at three-day intervals. The phage display peptide pe12-pal was tested also for longer-term efficacy in CIA, where it showed reduction of symptoms even when given at five-day intervals.

Therefore in some embodiments the isolated peptide or any functional derivatives or fragments thereof or pharmaceutical composition for use according to present disclosure is administered at one or more identical or different treatment periods of one, two, three or four weeks of once daily, once every three days, once every five days or once weekly administrations of said isolated peptide, wherein said treatment periods are consecutive or are set apart from each other by non-treatment intervals of 1 or several days such as 2, 3, 4, 5 or 6 days, or 1 or several weeks such as 1, 2, 3 or 4 weeks or 1, 2, 3 or more months.

In other embodiments the isolated peptide or any functional derivatives or fragments thereof or the pharmaceutical composition for use according to the present disclosure is administered at a single dose.

In further embodiments the isolated peptide or any functional derivatives or fragments thereof or pharmaceutical composition for use according to the present disclosure is administered at one or more treatment periods of one, two, three or four weeks of once daily administrations of a therapeutically effective amount of said isolated peptide.

In still further embodiments the isolated peptide or any functional derivatives or fragments thereof or pharmaceutical composition for use according to the present disclosure is for chronic administration.

In yet further embodiments the isolated peptide or any functional derivatives or fragments thereof or pharmaceutical composition for use according to the present disclosure is wherein said administration is once daily, once every three days, once every five days or once weekly.

Specific doses, route and frequency of administration are determined by the attending medical staff in accordance with good medical practice.

In some embodiments the isolated peptide or any functional derivatives or fragments thereof or pharmaceutical composition for use according to the present disclosure is for administration in combination with at least one additional therapeutically active agent.

The term "additional therapeutically active agent" as herein defined refers to an additional standard of care agent administered to a subject in need suffering from any of the non-pathogen associated inflammatory disorders as herein defined.

For example, an additional therapeutically active agent may be but is not limited to chemotherapy and anti-inflammatory agents (e.g. steroids and non-steroidal anti-inflammatory drugs). In the case of radiation-induced enteritis, the additional therapeutically active agent may include, but is not limited to ondansetron, loperamide, diphenoxylate and atropine, cholestyramine, sucralfate, and topical corticosteroids (hydrocortisone).

Thus in some embodiments the additional therapeutically active agent as herein defined is a steroid, a nonsteroidal anti-inflammatory agent or an immunosupressive agent.

In some other embodiments the isolated peptide or pharmaceutical composition according to the present disclosure and said at least one additional therapeutically active agent are administered simultaneously, or at different time points, in identical or different frequencies.

In further embodiments the isolated peptide or pharmaceutical composition according to the present disclosure is administered prior to or after administration of said at least one additional therapeutically active agent.

In still further embodiments the isolated peptide or pharmaceutical composition according to the present disclosure and the at least one additional therapeutically active agent as herein defined are administered for different durations of time.

In specific embodiments the isolated peptide or pharmaceutical composition for use according to the present disclosure is wherein said inflammatory disease or condition is rheumatoid arthritis and wherein said additional therapeutically active agent is selected from Abatacept, a TNF blocker, an IL-1 blocker, an IL-6 blocker and an Anti CD20 agent or a combination thereof.

In other specific embodiments the isolated peptide or pharmaceutical composition for use according to the present disclosure is wherein said inflammatory disease or condition is multiple sclerosis and wherein said additional therapeutically active agent is selected from interferon-β, Copaxone and Tysabri or a combination thereof.

In further specific embodiments the isolated peptide or pharmaceutical composition for use according to the present disclosure is wherein said inflammatory disease or condition is radiation-induced gastroenteritis and wherein said at least one additional therapeutically active agent is a chemotherapeutic agent.

The term "composition" or "pharmaceutical composition" as herein defined generally comprises an active agent being a peptide in accordance with the present disclosure and at least one of a buffering agent, an agent which adjusts the osmolarity thereof, and optionally, one or more pharmaceutically acceptable carriers, excipients and/or additives as known in the art. Supplementary active ingredients can also be incorporated into the compositions. The carrier can be solvent or dispersion medium containing, for example, water, ethanol, polyol (for example, glycerol, propylene glycol, and liquid polyethylene glycol, and the like), suitable mixtures thereof, and vegetable oils. Protease inhibitors may also be added.

In some embodiments the pharmaceutical composition for use according to the present disclosure comprises at least one physiologically compatible additive, carrier, diluent and excipient.

Thus, in yet a further aspect of the present disclosure, there is provided use of any and all of the above peptides and their functional derivative, in the preparation of pharmaceutical compositions for the treatment of any of the above non-pathogen induced inflammatory disorders, for example by admixing the peptide with at least one of said additives, carriers, diluents and excipients.

In a further aspect the present disclosure provides a method of treating a non-pathogen associated inflammatory disorder in a subject in need thereof, said method comprising administering to said subject a therapeutically effective amount of an isolated peptide which specifically binds to the crystallographic homodimer interface of CD28 or a functional derivative thereof, or a pharmaceutical composition comprising the same.

In this and all aspects of the present disclosure the said peptide can be any one of the peptides disclosed herein and their functional derivatives as herein defined.

Specific peptides are p2TA (SEQ ID NO: 4), (D-Ala)-p2TA-(D-Ala) (SEQ ID NO: 47), p2TB (SEQ ID NO: 9), (D-Ala)-p2TB-(D-Ala) (SEQ ID NO: 48), pe12 (SEQ ID NO: 12), (D-Ala)-pe12-(D-Ala) (SEQ ID NO: 49), and pal-pe12-(D-Ala) (SEQ ID NO: 51).

Also in this aspect, the method disclosed is intended for the treatment of radiation-induced inflammation, inflammatory bowel disease (IBD), radiation-induced gastroenteritis, drug-induced inflammation, arthritis, rheumatoid arthritis, osteoarthritis, lupus, myasthenia gravis, multiple sclerosis, adult respiratory distress syndrome (ARDS), asthma, rhinitis, idiopathic pulmonary fibrosis, peritonitis, cardiovascular inflammation, myocardial ischemia, reperfusion injury, atherosclerosis, trauma, diabetes type II, retinopathy, psoriasis, gastrointestinal inflammation, cirrhosis, appendicitis, bursitis, colitis, cystitis, dermatitis, phlebitis, vasculitis, acne vulgaris, and pelvic inflammatory disease.

The said drug-induced inflammation is any one of drug-induced hepatitis, drug-induced ocular inflammation, drug-induced gastrointestinal damage, drug-induced acute ulcers, drug-induced renal failure, drug-induced pancreatitis, drug-induced nephritis, chemotherapy-induced inflammation in the gastrointestinal tract and seborrheic keratosis.

A specific condition treated by the method of the invention is radiation-induced inflammation, which can be systemic and/or at the irradiated site. The radiation-induced inflammation can be associated with at least one of gastrointestinal tract and spleen inflammation.

Administration of the isolated peptide or composition comprising the same can be by a route selected from the group consisting of intravenous, intramuscular or intraperitoneal administration, intrathecal or subcutaneous injection, oral, intrarectal, intranasal ocular and topical administration.

In accordance with the disclosed method, the isolated peptide is administered at an amount of from about 0.05 mg to about 5.0 mg, for example 0.05, 0.1, 0.15, 0.2, 0.25, 0.3, 0.4, 0.5, 1.0, 2.0, 3.0, 4.0 or 5.0 mg peptide/kg body weight of the subject in need thereof. The said peptide can administered at one or more identical or different treatment periods of one, two, three or four weeks of once daily, once every three days, once every five days or once weekly administrations of said isolated peptide, wherein said treatment periods are consecutive or are set apart from each other by non-treatment intervals of 1 or several days, or 1 or several weeks or 1 or more months. The said peptide can also be administered at a single dose. Treatment can be by administration of the peptide to said subject in need at one or more treatment periods of one, two, three or four weeks of once daily administrations of a therapeutically effective amount of said isolated peptide. The disclosed method is suitable not only for treatment of acute inflammatory conditions, but also for chronic administration.

Thus, administration of the peptide or pharmaceutical composition comprising the same can be once daily, once every three days, once every five days or once weekly.

When treating radiation-induced inflammation, the peptide or pharmaceutical composition comprising the same can be administered to said subject at a suitable time prior to and/or post irradiation. The said peptide or pharmaceutical composition comprising the same can be administered to said subject immediately following, or within from about 30 minutes up to any time at which the radiation-induced inflammation persists, whether while the subject is still undergoing radiation therapy, in between radiation therapy treatments or thereafter. The peptide or pharmaceutical composition comprising the same can be administered to said subject in need from about 30 minutes to about 60 or 90 minutes, 2, 4, 6, 8, 10, 12, 14, 16, 18, 20, 22, 24, 36, 48, 60 or 72 hours, 4, 5, 6, 7, 14, 32 or 28 days following exposure to said radiation. Specifically, administration to said subject within about 24 hours following exposure to said radiation.

In accordance with the present disclosure, the disclosed peptides or pharmaceutical composition comprising the same can also be administered in combination with at least one additional therapeutically active agent. The additional therapeutically active agent can be at least one of a steroid, a nonsteroidal anti-inflammatory agent or an immunosupressive agent. The said peptide or pharmaceutical composition and said at least one additional therapeutically active agent can be administered simultaneously, or at different time points, in identical or different frequencies.

In a method for the treatment of, for example, rheumatoid arthritis, said additional therapeutically active agent is selected from Abatacept, a TNF blocker, an IL-1 blocker, an IL-6 blocker and an Anti CD20 agent or a combination thereof.

In a method for the treatment of, for example, multiple sclerosis, said additional therapeutically active agent is selected from interferon-β, Copaxone and Tysabri or a combination thereof.

In a method for the treatment of, for example, radiation-induced gastroenteritis, said at least one additional therapeutically active agent is a chemotherapeutic agent.

Disclosed and described, it is to be understood that this invention is not limited to the particular examples, methods steps, and compositions disclosed herein as such methods steps and compositions may vary somewhat. It is also to be understood that the terminology used herein is used for the purpose of describing particular embodiments only and not intended to be limiting since the scope of the present invention will be limited only by the appended claims and equivalents thereof.

It must be noted that, as used in this specification and the appended claims, the singular forms "a", "an" and "the" include plural referents unless the content clearly dictates otherwise.

Throughout this specification and the Examples and claims which follow, unless the context requires otherwise, the word "comprise", and variations such as "comprises" and "comprising", will be understood to imply the inclusion of a stated integer or step or group of integers or steps but not the exclusion of any other integer or step or group of integers or steps.

The following examples are representative of techniques employed by the inventors in carrying out aspects of the present invention. It should be appreciated that while these techniques are exemplary of preferred embodiments for the practice of the invention, those of skill in the art, in light of the present disclosure, will recognize that numerous modifications can be made without departing from the spirit and intended scope of the invention.

EXAMPLES

Without further elaboration, it is believed that one skilled in the art can, using the preceding description, utilize the present disclosure to its fullest extent. The following preferred specific embodiments are, therefore, to be construed as merely illustrative, and not limitative of the claimed invention in any way.

Standard molecular biology protocols known in the art not specifically described herein are generally followed essentially as in Sambrook & Russell, 2001.

Standard medicinal chemistry methods known in the art not specifically described herein are generally followed essentially in the series "Comprehensive Medicinal Chemistry" by various authors and editors, published by Pergamon Press.

Experimental Procedures

Peptide Synthesis

The peptides described herein were synthesized using fluoronyl-methoxycarbonyl chemistry, cleaved and the side chain deprotected with triflouroacetic acid. Peptides were >95% pure by high-pressure liquid chromatography and their molecular weight was verified by MALDI-TOF mass spectrometry. The peptides were abutted with D-Alanine (D-Ala) at both termini for greater protease resistance in biological assays (5, 6) and with Cysteine (Cys) for surface plasmon resonance spectroscopy. Where indicated, palmitoyl-lysine (pal) was linked to the N-terminus of the peptide instead of D-Ala. For the CD28 affinity selection of pe12, the PhD-12 combinatorial phage display library of M13KE (New England Biolabs) was panned on immobilized CD28-Fc following the manufacturer's instructions. After 4 rounds of panning, phages were immobilized on nitrocellulose membranes and incubated with 0.5 µg/ml horseradish peroxidase-conjugated CD28-Fc (R&D Systems); >10% of selected phages tightly bound CD28-Fc.

Peptide Sequences

The peptide having the amino acid sequence of SPMLVAYD (denoted by SEQ ID NO. 4), corresponding to residues 8-15 of the extracellular domain of CD28, was abutted by D-Ala amino acid residues at both its termini, as described above and is denoted herein by SEQ ID NO. 47 and termed herein "p2TA". The peptide having the amino acid sequence of PAVVLASS (denoted by SEQ ID NO. 9), corresponding to residues 8-15 of the extracellular domain of CTLA-4 homodimer interface was abutted by D-Ala amino acid residues at both its termini and is denoted herein by SEQ ID NO. 48 and termed herein "p2TB". The peptide having the amino acid sequence SHFTHNRHGHST, denoted by SEQ ID NO. 12, was selected from a 12-mer phage display library for affinity for the extracellular domain of CD28, as detailed above. This peptide was abutted by D-Ala amino acid residues at both its termini and is denoted herein by SEQ ID NO. 49 and termed herein "pe12". Various of the peptides were also abutted by palmitoyl-lysine (pal) instead of D-Ala at their N-terminus. SEQ ID NO. 50 and SEQ ID NO. 51 denotes palmitoyl-lysine at the N-termini of the peptides p2TB and pe12, respectively and these peptides are termed herein p2TB-pal and pe12-pal, respectively.

TABLE 1

Peptide sequences

| SEQ ID NO. | Sequence | Name |
|---|---|---|
| 48 | (D-A)PAVVLASS(D-A) | (D-A)-p2TB-(D-A) |
| 50 | (palmitoyl-lysine)PAVVLASS(D-A) | pal-p2TB-(D-A) |
| 49 | (D-A)SHFTHNRHGHST(D-A) | (D-A)-pe12-(D-A) |
| 12 | SHFTHNRHGHST | pe12 |
| 51 | (palmitoyl-lysine)SHFTHNRHGHST(D-A) | pe12-pal |
| 4 | SPMLVAYD | p2TA |
| 47 | (D-A)SPMLVAYD(D-A) | (D-A)-p2TA-(D-A) |
| 9 | PAVVLASS | p2TB |
| 52 | (D-A)ASMDYPVL(D-A) | p2TAsc-(D-A) |

Induction of Cytokine Expression

Peripheral blood mononuclear cells (PBMC) from healthy human donors were separated on Ficoll Paque (Amersham), washed twice with 50 ml of RPMI 1640 medium, resuspended at a density of $4 \times 10^6$ cells/ml and cultured in this medium supplemented with 2% fetal calf serum, 2 mM glutamine, 10 mM Minimum Essential Medium (MEM) nonspecific amino acids, 100 mM Na-pyruvate, 10 mM Hepes pH 7.2, $5 \times 10^{-5}$ M 2-mercaptoethanol, 100 u/ml penicillin, 100 µg/ml streptomycin and 5 µg/ml nystatin. Mouse anti-human monoclonal antibodies αCD3 (clone UCHT1; 100 ng/ml) and αCD28 (clone 37407; 2.5 µg/ml) (both from R&D Systems) were used as inducers. Cytokines in culture medium were determined with Quantikine ELISA kits (R&D Systems) according to the manufacturer's instructions.

Surface Plasmon Resonance Spectroscopy

Peptides were diluted to 10-200 µg/ml in 10 mM Sodium (Na) acetate pH 4.0 and immobilized on a CM5 sensor chip (BIAcore) using an amine-thiol coupling kit (BIAcore), respectively; the immobilized amounts were 500-1,000 resonance units. Analytes were injected at 20 µl/min in 25 mM HEPES pH 7.4, 150 mM NaCl, 3.4 mM EDTA, and 0.005% surfactant P20 under conditions showing no mass transport limitation. Regeneration was with 50 mM phosphoric acid. Kinetic analyses were performed at 25° C. in a BIAcore 3000 instrument, deducting the signal from the control flow cell from the binding signal. Analyte curves were run in duplicate; representative results are shown. Human IgG (Jackson Laboratories) served as control. Fusion of the IgG1-Fc domain to the 152-amino-acid extracellular domain of CD28 was performed as described below.

B7-2 Expression Vectors

A vector expressing B7-2 was generated by cDNA synthesis of human CD86 (NM_175862) from total human PBMC RNA using Verso RT-PCR kit (ABgene). CD86 cDNA was generated using KOD polymerase (Novagen) with the phosphorylated PCR primers 5'-GACGTCGACG-GAAGGCTTGCACAGGGT (denoted by SEQ ID NO: 53) and 5'-CACGCGGCCGCCCAGGTCATGAGCCAT-TAAGC (denoted by SEQ ID NO: 54). The PCR product was inserted into pEGFP-N3 DNA (Clontech) that had been digested with SalII and NotI and lacked the GFP region, using Fast-Link DNA Ligation Kit (Epicentre). Vectors expressing B7-2 fused C-terminally to GFP or Cherry were generated from B7-2 cDNA vector template with phosphorylated PCR primers 5'-TACTCGAGATGGGACTGAG-TAACATTC (denoted by SEQ ID NO: 55) and 5'-GTC-CGCGGTGAAGCATGTACACTTTTGTCG (denoted by SEQ ID NO: 56), deleting the B7-2 termination codon. Upon digestion with XhoI and SacII, the PCR product was inserted either into pEGFP-N3 DNA or pmCherry-N1 DNA (Clontech). B7-2C/Cherry vector was generated from B7-2/Cherry template using primers 5'-GTCTCTCGTCCTTC-CGG (denoted by SEQ ID NO: 57) and 5'-CTAACTTCA-GTCAACCTG (denoted by SEQ ID NO: 58). The above primers are listed in Table 2 below.

TABLE 2

PCR primers

| SEQ ID NO: | Sequence |
|---|---|
| 53 | GACGTCGACGGAAGGCTTGCACAGGGT |
| 54 | CACGCGGCCGCCCAGGTCATGAGCCATTAAGC |
| 55 | TACTCGAGATGGGACTGAGTAACATTC |
| 56 | GTCCGCGGTGAAGCATGTACACTTTTGTCG |
| 57 | GTCTCTCGTCCTTCCGG |
| 58 | CTAACTTCAGTCAACCTG |

CD28/B7-2 Interaction

In order to assay the effect of p2TA on binding of B7-2 to CD28 on a cell, HEK293T cells were transfected to express cell-surface CD28, as described in Arad et al., 2011 (3) or with an empty vector expressing GFP. After 36 hours, the cells were incubated for 45 min with 0.2 μg/ml soluble B7-2 in the absence or in the presence of (D-A)-p2TA-(D-A). After three washes with cold phosphate-buffered saline, the cells were lysed. Equal amounts of total cell protein (as determined by a Bradford assay) were subjected to 10% PAGE and Western blotting to show binding of B7-2 and expression of CD28 by the cells. Conversely, the effect of p2TA on binding of CD28 to B7-2 on the cell was assayed by transfecting HEK293T cells to express cell-surface B7-2. After 36 hours, the cells were incubated for 45 min with 0.2 μg/ml soluble CD28 in the absence or presence of (D-A)-p2TA-(D-A). After three washes as described above, the cells were lysed and equal amounts of total cell protein were subjected to 10% PAGE and Western blotting to show binding of CD28 and expression of B7-2 by the cells.

For the flow cytometry assays, vectors expressing CD28/GFP (3) and B7-2/Cherry fusion proteins that leave the extracellular ligand binding domains intact were used. HEK293T cells, separately transfected to express CD28/GFP (green) and B7-2/Cherry or B7-2C/Cherry (red), and upon addition of 10 mM EDTA were co-incubated in the absence or presence of (D-A)-p2TA-(D-A) for 2 hours at room temperature at a concentration of $10^5$ cells ml$^{-1}$ each. Synapse formation between cell populations was analyzed by flow cytometry (Eclipse Flow Cytometry System, Sony), scoring the percentage of events positive for green and red using FlowJo vX.0.6 software.

Soluble B7-2 and CD28

B7-2-Fc and CD28-Fc expressed in mouse myeloma NS0 cells (R&D Systems) comprise the extracellular 20-239 and 19-152 amino acid domain, respectively, of the mature human ligands fused to C-terminal human IgG1 Fc and are homodimers, disulfide-linked in the Fc domain Soluble ligands were >95% pure as judged by SDS-PAGE.

Adjuvant Arthritis Model

Female Lewis rats (Harlan, Israel, 8 weeks of age) were injected sub-cutaneousely (SC) on day 1 into the base of their tail with 1 mg *Mycobacterium tuberculosis* (MT) HR37 (DIFCO—Cat.No 231141) suspended into 0.1 ml of incomplete Freund's adjuvant, an accepted model for induction of adjuvant arthritis. Peptides, phosphate-buffered saline (PBS) or dexamethasone were injected intravenously (IV). Rats were weighed weekly, and overall health status noted. Rats were monitored by daily examination for the onset of disease, which was recorded. Clinical score was determined by swelling of the joints on a scale of 1-4 per limb, with a maximal total score/animal reaching 16.

Collagen-Induced Arthritis Model

Male DB1 mice (Harlan, Israel, 8 weeks) were used to elicit collagen-induced arthritis by SC injection on days 0 and 21 of 0.05 ml of a mixture containing 0.5 mg type II collagen from calf joints, dissolved in 0.1 molar acetic acid mixed 1:1 with 1.5 mg/ml complete Freund's Adjuvant emulsion into the base of their tail. Peptide, PBS or dexamethasone was administered daily from the disease onset until termination. Mice were weighed weekly, and their overall health status was noted. Mice were monitored by daily examination for the onset of disease, which was recorded. Clinical score was determined by swelling of the joints on a scale of 1-4 per limb, with a maximal total score/animal reaching 16.

Experimental Autoimmune Encephalitis (EAE) Model

Female C57 Black/6 mice (Harlan) 8 weeks of age were used. MOG peptide 35-55 (Sigma) solution was prepared freshly prior to each inoculation session by dissolving the reverse phase high performance liquid chromatography (RP-HPLC)-purified lyophilized powder in PBS to achieve a solution at a final concentration of 2.5 mg/ml mixed with complete Freund's adjuvant suspension, containing killed *M. tuberculosis* HR37 (DIFCO—Cat.No 231141) at a concentration of 4 mg/ml; 200 μl of this solution was injected SC into the right flank of the mice on day 0 and into the left flank on day 7. Pertussis toxin (200 ng) was injected intraperitoneal (IP) on days 0 and 2. Peptide or PBS was injected SC on the back of the mice. Solumedrol (SOLU-MEDROL 500 mg, Pfizer) was injected IV. Mice were weighed weekly, and their overall health status was noted. Mice were monitored by daily examination for the onset of disease, which was recorded. Encephalitic score was measured by observation of paralysis: score 1, tail paralysis; score 2, back limbs paralysis; score 3, front limbs paralysis; score 4, total body paralysis; score 5, mortality.

Pharmacokinetic Assay

Analysis was performed by reverse phase liquid chromatography with mass spectrometric detection. An Agilent 1100 MSD system with temperature-controlled autosampler was used. The system was calibrated using purified (D-A)-p2TA-(D-A) (molecular weight, 1,037.2 g/mol, Bachem) and blank mouse plasma (Harlan, Israel) as reference.

GLP Toxicology Studies

Nonclinical toxicology, immunotoxicology and neurotoxicology studies with p2TA in mice and pigs were conducted in accordance with good laboratory practices (GLP) guidelines.

Statistical Methods

For each animal model, pair-wise comparisons were performed, comparing for each peptide treated and untreated groups. The repeated measures ANOVA model was applied to the data in order to assess the significance of trend over time, the difference between the study groups, and the interaction between time and treatment. The Greenhouse-Geisser test was used to assess the significance of the trend and the interaction. The test was two-tailed; $P \leq 0.05$ was considered statistically significant.

Irradiation Experiments

Mice

Eight weeks old male mice of BALB/c and A/J strains were obtained from Jackson Laboratories (Bar Harbor, Me.). Mice received rodent chow (Harlan Teklad, Wis.) and water ad libitum. Housing and experiments were carried out with institutional Animal Care and Use Committee approval. Two inbred strains of mice, BALB/c ad A/J, were selected for this study because of their innate differences in radiosensitivity. Specifically, the jejunal crypt cells of BALB/c mice were found to be more radiosensitive than those of A/J animals. Eight animals were exposed to 8 Gy of total-body irradiation, where four of these animals were injected with (D-A)-p2TA-(D-A) peptide 24 hours post irradiation (the group termed "RP") in order to evaluate whether (D-A)-p2TA-(D-A) peptide can mitigate the effects of radiation. The group of mice exposed to 8 Gy of total-body irradiation and not treated with the peptide was termed "R", sham-irradiated mice (control) were termed "C" and sham-irradiated mice that received 5 mg/kg of the (D-A)-p2TA-(D-A) peptide were termed "P". Seven days post irradiation, a time-point associated with a pronounced IL-6 and COX-2 expression in plasma and tissues of irradiated animals, the mice were sacrificed.

Irradiation Procedure

Eight mice of each strain were given a single total-body radiation dose of 8 Gy cesium 137 (Cs-137) gamma rays, at a dose rate of 95.7 cGy/min (Best Theratronics, Ottawa, Canada). Sham-irradiated animals were treated in the same manner but were not exposed to the source and served as control animals. Twenty four hours later, half of the sham- and 8Gy-irradiated mice were injected with (D-A)-p2TA-(D-A) peptide (5 mg/kg) via tail vein injection, Animals were sacrificed by $CO_2$ asphyxiation followed by cervical dislocation 7 days after irradiation (namely 6 days after peptide injection).

Measurement of Pro-Inflammatory Mediators in Irradiated Mice

Blood samples were collected immediately after sacrifice by intracardiac puncture. The concentration of Interleukin 6 (IL-6) in diluted plasma (1:3) was determined using a specific ELISA kit (IL-6, eBioscience, San Diego, Calif.). Fibrinogen concentration determination in plasma samples diluted 1:20,000 was performed using a specific ELISA kit (Immunology Consultants Laboratory, Portland, Oreg.). Recombinant mouse IL-6 and fibrinogen were used as standards.

Immunohistochemistry in Irradiated Mice

The mid-jejunum of the small intestine and spleen tissues were dissected, fixed in 10% buffered formalin, embedded in paraffin, and sectioned at 4 μm thin sections. Slides were stained by hematoxylin and eosin (H&E); immunohistochemistry was performed at the Northwestern University Mouse Histopathology Core Facility with in-house developed antibodies directed against COX-2, cyclin D1 and macrophage marker F4/80. Slides were imaged using a TissueGnostic microscope (Zeiss, Oberkochen, Germany) Quantification of the immunohistochemistry results was done with HistoQuest software.

Histopathological Analysis of Small Intestine of Irradiated Mice

Intestinal damage was assessed by measurements of villus height and the numbers of surviving crypts in each circumference using H&E-stained jejunal slides. Villus height was measured from the bottom of the crypt to the crypt-villus junction. The number of surviving crypts was determined using the criteria that a surviving crypt must contain at least 10 epithelial cells, at least one Paneth cell and a lumen. Four circumferences were scored per mouse in each group. The viability of surviving crypts was confirmed by immunohistochemical detection of cyclin D1.

Immunohistochemistry of Activated Macrophage Marker F4/80 in Mouse Jejunum

Jejunal tissues were collected 7 days after irradiation and embedded in paraffin. After fixation and processing, cross sections of jejunum were immunostained with F4/80 antibodies and the number of F4/80 positive cells per $mm^2$ area of tissue was counted using the HistoQuest image analysis software. Bars represent the means±SEMs for tissue sections of mice in each group. *Statistically significant differences between R and RP groups (P<0.05).

Antibodies

Horseradish peroxidase-conjugated goat anti-mouse IgG or donkey anti-goat (KPL), mouse monoclonal αCD28 (clone 37407), αCD3 (clone UCHT1), goat polyclonal anti-CD28 and anti-B7-2 (R&D Systems) antibodies were used.

Data Analysis

Data collected from all the irradiated (or sham-irradiated) animals in the group were pooled and presented as means+/−SEM. Statistical analyses were performed by analysis of variance and the t-test. A P value of less than 0.05 indicated statistical significance.

Example 1

Inhibition of CD28 Signaling

As indicated above, it was reported that short peptides can prevent CD28 signaling induced by pathogenic exogenous stimuli, for example toxins and bacteria. Specifically, it has been shown that the peptide p2TA, which is an octapeptide mimetic of the CD28 homodimer interface, prevents the engagement of CD28 by superantigens in vivo. Therefore, inhibition of CD28 signaling was first examined for peptide mimetics of the CD28 and CTLA-4 homodimer interface, as described below.

The octapeptides having the amino acid sequence SPM-LVAYD (denoted by SEQ ID NO. 4) and PAVVLASS (denoted by SEQ ID NO. 9) and the peptide pe12 having the amino acid sequence SHFTHNRHGHST (denoted by SEQ ID NO. 12) prepared as described above, were abutted at both ends by D-Ala residues. The peptides obtained are denoted herein by SEQ ID NO. 47 ((D-A)-p2TA-(D-A)), SEQ ID NO. 48 ((D-A)-p2TB-(D-A)) and SEQ ID NO. 49 ((D-A)-pe12-(D-A)).

As demonstrated in FIG. 1, in human PBMC, the peptides p2TA, p2TB and pe12 (SEQ ID NO: 47 48, 49, respectively) did not inhibit the αCD3-mediated induction of IL2 and TNF-α. In addition, these peptides did not inhibit the αCD3-mediated induction of the Th1 cytokines IFN-γ (FIG. 2A), showing that they do not block signaling through the T cell receptor.

However, each of these peptides strongly inhibited the production of IFN-γ, IL2 and TNF-α when secretion of these cytokines was induced by αCD3 jointly with αCD28, as shown in FIG. 2B, FIG. 2C and FIG. 2D, respectively). As demonstrated in FIG. 3A, FIG. 3B and FIG. 3C, by themselves, these peptides did not elicit significant levels of IFN-γ, IL2 or TNF-α, respectively. Thus, these peptides inhibit signaling for an inflammatory cytokine response when it is transduced through CD28.

Example 2

Binding of the Peptides to CD28

Figure 5A:
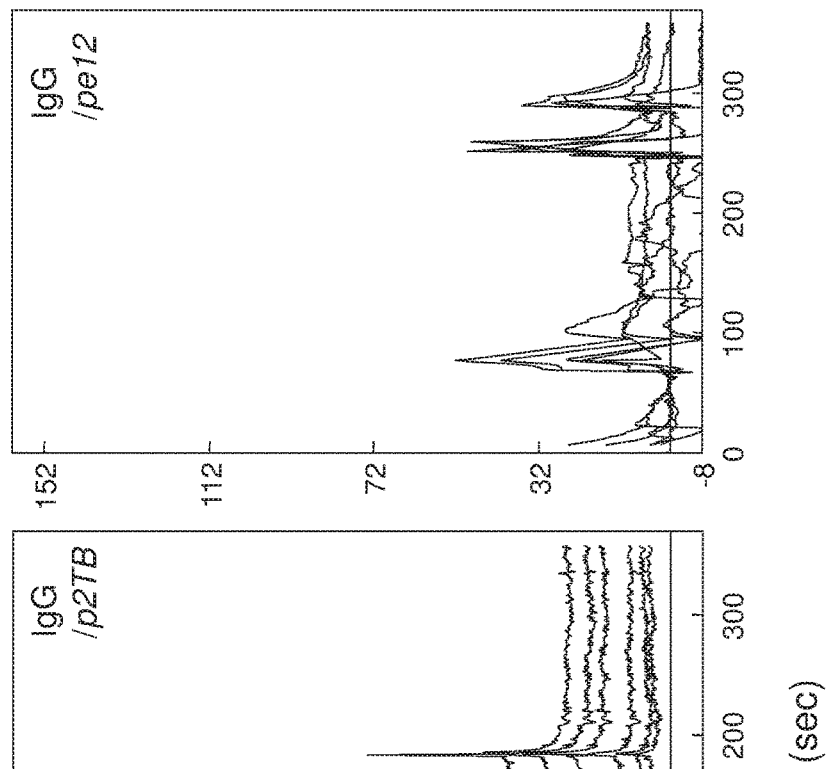
FIG. 5A-5C: The peptides do not bind significantly to IgG. Graphs showing representative SPR responses for binding of human IgG to immobilized p2TA (FIG. 5A), p2TB (FIG. 5B) and pe12 (FIG. 5C). Analyte concentrations increased in twofold increments from 0.2 μM (FIG. 5A, FIG. 5B) and 0.125 μM (FIG. 5C).
Figure 5B:
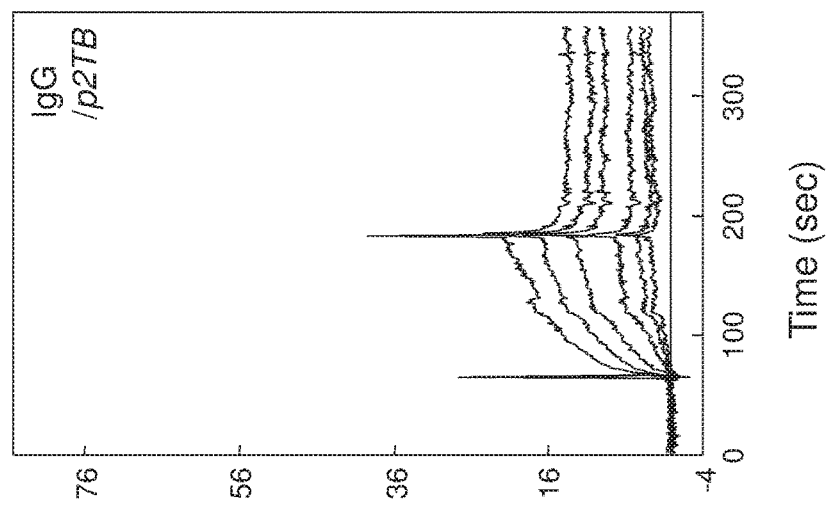
Figure 5C:
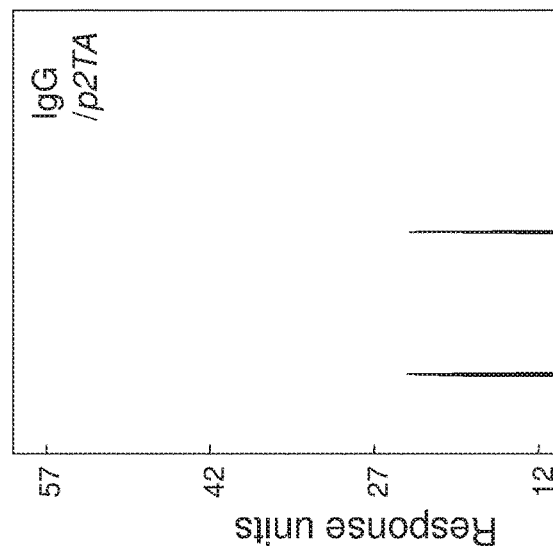
Figure 6A:
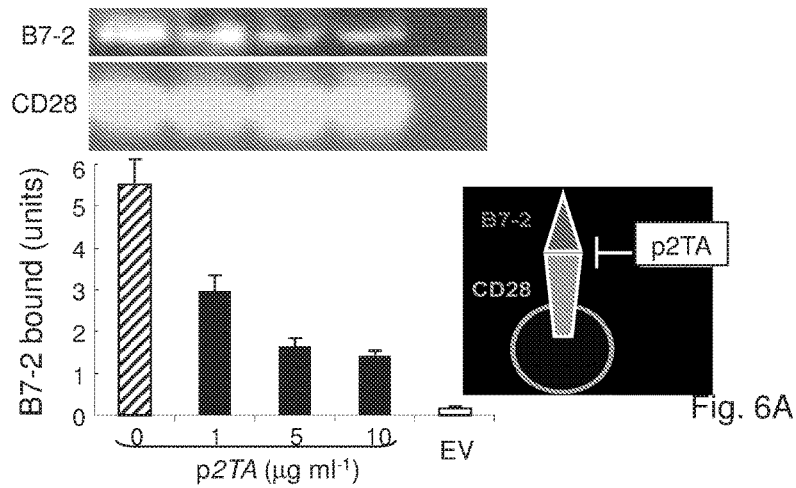
FIG. 6A-6H: CD28 dimer interface mimetic peptide p2TA inhibits synapse formation between the co-stimulatory receptors B7-2 and CD28.
Figure 6B:
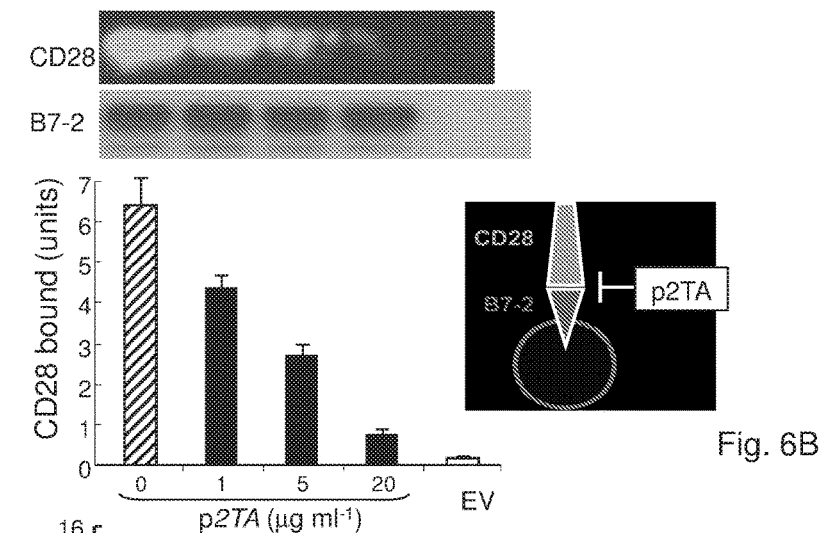
Figure 6C:
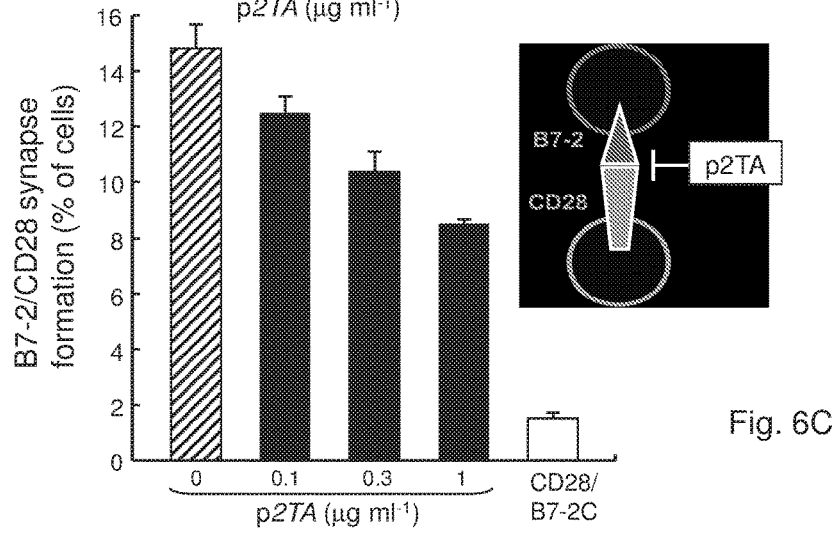
Figure 6D:
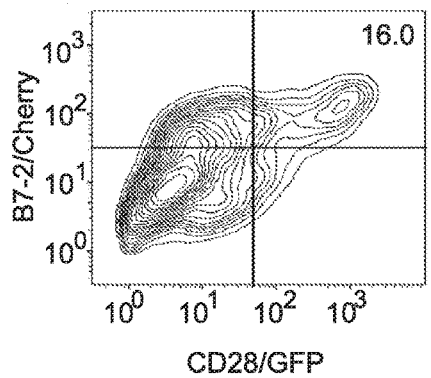
Figure 6E:
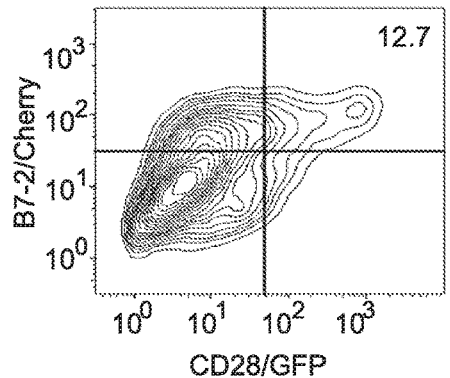
Figure 6F:
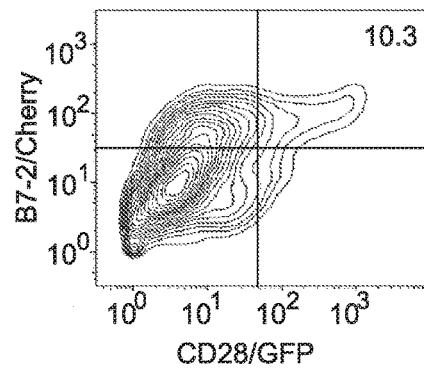
Figure 6G:
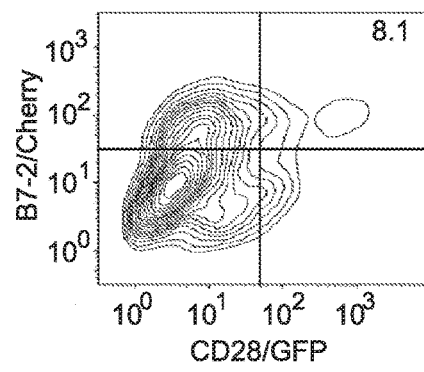
Figure 6H:
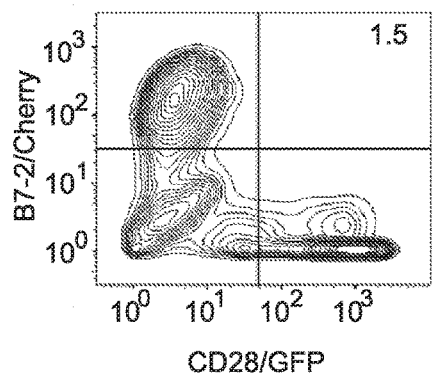
Figure 7:
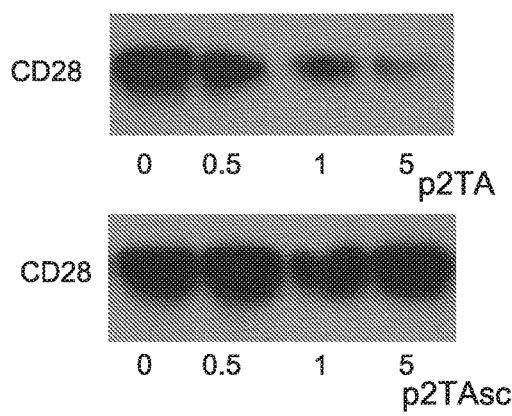
FIG. 7: Random scrambling of p2TA sequence abrogates its ability to inhibit the B7-2/CD28 interaction. Western blot analyses of HEK293T cells transfected to express cell-surface B7-2 and incubated with soluble CD28 in the absence or presence of (D-Ala)-p2TA-(D-Ala) or its scrambled form p2TAsc ((D-A)ASMDYPVL(D-A)) at the indicated concentrations. Equal amounts of total protein (Bradford assay) were subjected to 10% PAGE and western blotting to show binding of CD28 by the cells.

As shown by plasmon resonance spectroscopy analysis conducted as described above and shown in FIG. 4, immobilized p2TA, p2TB and pe12 (SEQ ID NO: 47 48, 49, respectively) each bound directly to soluble CD28, comprised of its 152-amino-acid extracellular domain fused to an IgG1-Fc dimer (CD28-Fc). This binding was specific, as none of the peptides showed affinity for IgG studied in parallel (FIG. 5). The data yielded an apparent $K_D$ for binding of p2TA, p2TB and pe12 (SEQ ID NO: 47 48, 49, respectively) to CD28-Fc in the micromolar range.

Example 3 p2TA Attenuates the Interaction Between B7-2 and CD28 Costimulatory Ligands

The CD28 dimer interface mimetic peptide p2TA was designed to be a superantigen toxin antagonist that by binding to the superantigen prevents it from binding to CD28 and thereby from inducing a harmful pathogen-induced inflammatory cytokine response (3). Therefore, the results presented in FIG. 4A, namely the finding that p2TA binds directly to CD28, was unexpected.

As known in the art, formation of the B7-2/CD28 costimulatory axis is critical for full T-cell activation resulting in an inflammatory cytokine response. In order to examine the possibility that binding of p2TA to CD28 might affect its ability to interact with B7-2, CD28 and B7-2 were each separately expressed on the cell surface of cells and the effect of p2TA on binding of B7-2 and CD28 was studied. This strategy allowed for monitoring the B7-2/CD28 interaction in the absence of multiple ligand-receptor interactions that underlie synapse formation between the antigen-presenting cell and the T cell, involving not only MHC-II/TCR interaction but also numerous costimulatory ligand pairs (CD28, CTLA-4, CD40, PD-1, ICOS, B7-1, B7-2, etc.), that would mask the contribution of B7-2/CD28 engagement.

Surprisingly, as shown in FIG. 6A, p2TA (SEQ ID NO: 47) strongly inhibited the binding of soluble B7-2 to cell-surface CD28. In addition, as shown in FIG. 6B, binding of soluble CD28 to cell-surface B7-2 was inhibited by an order of magnitude by p2TA. This inhibitory activity of p2TA was sequence-specific, as verified by scrambling of the amino acid sequence of p2 TA. Random scrambling of the amino acid sequence of p2TA (namely (D-A)SPMLVAYD(D-A)), denoted by SEQ ID NO: 47 to (D-A)ASMDYPVL(D-A), denoted by SEQ ID NO. 52, which was previously shown to strongly impair the ability of p2TA to bind directly to the superantigen, staphylococcal enterotoxin B (SEB), and to protect mice from lethal SEB challenge (3), also fully abrogated the ability of p2TA to inhibit the B7-2/CD28 interaction, shown by loss of the ability to inhibit binding of CD28 to cell-surface B7-2 (FIG. 7).

Next, flow cytometry was used in order to validate that p2TA attenuates B7-2/CD28 synapse formation occurring between cells that express B7-2 and CD28, respectively, on their surface (FIG. 6C). B7-2C, a splice variant of B7-2 that is unable to bind CD28, failed to support significant intercellular synapse formation, demonstrating specificity. Remarkably, even though flow cytometry will not distinguish a synapse formed by a single intercellular B7-2/CD28 pair from one supported by multiple pairs, rendering it less sensitive than binding of the soluble coreceptors, p2TA had a pronounced inhibitory effect on intercellular B7-2/CD28 synapse formation, observed already at low p2TA concentrations (FIG. 6C-FIG. 6H).

Example 4

Effect of the Peptides on Adjuvant Arthritis

The ability of the peptides to suppress symptoms of an autoimmune disease caused by excessive production of inflammatory cytokines, including IFN-γ, IL2 and TNF-α was examined in the rat adjuvant arthritis model, in which arthritis was induced by exposure to *Mycobacterium tuberculosis*, as described above.

In this model, symptoms appear after about ten days and maximal joint swelling is evident by day 20 (FIG. 8). As demonstrated in FIG. 8A and FIG. 8B, disease symptoms were suppressed almost in full by daily treatment with dexamethasone from day 10 to day 15. By contrast, daily treatment with the peptides (D-A)-p2TA-(D-A) (denoted by SEQ ID NO: 47) or (D-A)-pe12-(D-A) (denoted by SEQ ID NO: 49) from day 1 to day 15 did not exhibit inhibition of symptoms over the time interval up to day 15 (FIG. 8A, FIG. 8B, respectively).

However, a major difference was revealed when therapy was terminated on day 15. While a prompt and essentially complete rebound to maximal disease symptoms occurred in the steroid-treated animals between days 15-34 (namely animals treated by dexamethasone), the symptoms leveled off and even showed a progressive further decline in the animals that were treated with the peptide ((D-A)-p2TA-(D-A) (denoted by SEQ ID NO: 47) or (D-A)-pe12-(D-A) (denoted by SEQ ID NO: 49)), lasting through a two-week period after termination of treatment. In each case, symptoms declined below those seen for the animal group that was previously treated by dexamethasone.

Thus, as evident from FIG. 8, treatment with the peptides p2TA or pelt (SEQ ID NO: 47 or 49, respectively) during days 1-15 yielded a cumulative reduction of disease symptoms of 51% and 41%, respectively, which extends beyond the days of treatment. For both peptides, a significant difference between the peptide and the untreated groups was demonstrated, as well as a significant interaction between time and treatment.

The long-term efficacy of the peptides was surprising because short peptides have a short half-life (of minutes) in the circulation, owing to their rapid secretion by the kidney and their attack by proteases. Indeed, a pharmacokinetic analysis of p2TA in the blood circulation of mice showed that the peptide was detected in the serum by 1 min after injection, but became undetectable within 5 min (FIG. 9).

Example 5

Effect of the Peptides on Collagen-Induced Arthritis (CIA)

Arthritis induced in mice upon collagen exposure, performed as described above, more closely approximates rheumatoid arthritis in humans. In this model, treatment was started only once symptoms had appeared (disease onset), namely on day 25.

As shown in FIG. 10, although the clinical score of the disease was still on the increase at the end of the monitoring period (day 33, namely day 11 after the disease onset), the peptide p2TA (SEQ ID NO: 47) significantly reduced the disease manifestation when given daily from disease onset, with cumulative symptoms decreasing by 59%, as demonstrated in FIG. 10A.

The ability of p2TB (SEQ ID NO: 9) and p2TB-pal, to which a palmitoyl-lysine residue was added at its N-terminus (SEQ ID NO. 50) to reduce CIA when given only once every three days was then examined. As shown in FIG. 10A, this treatment resulted in reduction of cumulative disease symptoms by 39% and 34%, respectively. These results were highly significant.

The long-term efficacy of the peptides was reinforced by an independent experiment shown in FIG. 10B, where a pe12-pal peptide (having the amino acid sequence palmitoyl-lysine-SHFTHNRHGHST, denoted by SEQ ID NO. 51) ameliorated the disease symptoms by 31% when given every three days and by 27% when given as much as five days apart.

Taking together the difference between the results obtained for the peptides and the untreated groups, as well as the interaction between time and treatment, the results reported in FIG. 10 were highly significant.

Example 6

Effect of the Peptides on Experimental Autoimmune Encephalitis (EAE)

EAE in the mouse is an established model of multiple sclerosis. In this model system, symptoms appear around day 10 after disease induction and increase up to day 30 (see for example FIG. 11A). EAE was induced in mice as described above.

In order to examine the effect of the peptides in the EAE model, peptides or the steroid solumedrol were daily administered from day 1 to EAE-induced mice, as described above. As demonstrated in FIG. 11, solumedrol reduced the cumulative disease symptoms by 50%. Measured against this standard, the peptides p2TB and pe12-pal (denoted by SEQ ID NO: 9 and SEQ ID NO: 51) had a pronounced suppressive effect on disease symptoms, significantly reducing the cumulative clinical score by 58% and 63%, respectively (FIG. 11A).

In an independent experiment, the peptides were given either once a day or, at a higher dose, or once every three days, as demonstrated in FIG. 11B, FIG. 11C and FIG. 11D. Solumedrol again yielded a 50% reduction in the cumulative clinical score. As shown in FIG. 11B, the peptide p2TB (SEQ ID NO:48) reduced the clinical score by 36% when given daily and by 34% when given at 3-day intervals.

By comparison, the peptide p2TB-pal (denoted by SEQ ID NO. 50), administered at the same doses, yielded a reduction in the cumulative clinical score of 41% when given daily and of 31% when given once every three days. Interestingly, a fivefold lower daily dose of p2TB-pal still yielded a reduction of 38%, as shown in FIG. 11C.

Finally, when given at 3-day intervals, the peptide pe12-pal (denoted by SEQ ID NO. 51) yielded a 48% reduction in cumulative symptoms, an efficacy even exceeding that seen upon daily dosing, namely a 42% reduction (FIG. 11D). These results were highly significant, providing strong evidence of long-term efficacy.

Example 7

Effect of the p2TA Peptide on Plasma Proteins Following Whole Body Gamma Irradiation As indicated above, exposure to ionizing radiation (IR) promotes inflammatory reactions, which may be manifested for example by excessive gastrointestinal (GI) inflammatory responses and pulmonary injury following exposure to radiation.

The effect of the peptide (D-Ala)-p2TA-(D-Ala) (denoted by SEQ ID NO: 47) on irradiated mice was thus further examined in a radiation-induced inflammation animal model, as described above. The effect was assessed based on the levels of IL-6, and fibrinogen, all of which are considered as pro-inflammatory mediators.

Cytokine interleukin 6 (IL-6) is an important mediator of the acute phase of protein expression and hematopoietic cell production. A shown in FIG. 12A, when measured seven days after exposure to radiation, IL-6 had increased significantly in the plasma of mice that were exposed to radiation as described above, consistent with previous reports. FIG. 12A demonstrates that IL-6 levels were enhanced 6.9- and 8.9-fold in the plasma of irradiated mice, respectively, in BALB/c and A/J mice ($P<0.05$, R vs. C group). Injection of sham-irradiated mice with the (D-Ala)-p2TA-(D-Ala) peptide did not affect IL-6 levels (FIG. 12A). However, as shown in FIG. 12A, treatment of irradiated mice with (D-Ala)-p2TA-(D-Ala) resulted in a significant inhibition of IL-6, 40.4% in BALB/C and 31.8% in A/J mice compared to irradiated mice ($P<0.05$; PR vs. R group).

As shown in FIG. 12B, the fibrinogen levels in irradiated BALB/c and A/J mice were increased 1.6- and 2.5-fold, respectively, compared to sham-irradiated animals. Injection of sham-irradiated mice with the (D-Ala)-p2TA-(D-Ala) (SEQ ID NO: 47) peptide did not affect fibrinogen levels significantly. However, in irradiated mice, a significant decrease in fibrinogen plasma levels was observed in mice treated with the (D-Ala)-p2TA-(D-Ala) peptide, as demonstrated in FIG. 12B. Fibrinogen levels in irradiated and (D-Ala)-p2TA-(D-Ala) treated mice were 67.5% (BALB/c) and 62.9% (A/J) of fibrinogen levels in irradiated counterparts ($P<0.05$; PR vs. R group) (FIG. 12B).

Example 8 p2TA Peptide Protects the Small Intestine from Radiation-Induced Damage

It is known that the number of jejunal crypts following whole-body irradiation correlates with animal survival. Therefore, the number of jejunal crypts following whole-body irradiation was counted on hematoxylin and eosin (H&E) stained slides following a defined protocol. As shown in FIG. 13A, the number of crypt microcolonies increased significantly in intestines of radiation and (D-Ala)-p2TA-(D-Ala) peptide-treated (PR) mice compared with intestines from irradiated (R) mice. Specifically, in BALB/c mice, the number of microcolonies elevated from $6.5\pm1.3/\mu m$ in the R group to $12.4\pm3.2/\mu m$ in the RP group ($P<0.05$). In A/J mice, the number of microcolonies elevated from $7.8\pm1.6/\mu m$ in the R group to $12.1\pm2.1/\mu m$ in the RP group ($P<0.05$).

Villus height in jejunal cross sections is another hallmark of gastrointestinal tract (GI) injury. As shown in FIG. 13B, the mean villus height was $192\pm41$ μm for control BALB/c and $208\pm45$ μm for control A/J mice. In irradiated mice, the mean villus height decreased to $86\pm25$ μm for BALB/c and $122\pm22$ μm for A/J mice. Interestingly, administration of the (D-Ala)-p2TA-(D-Ala) peptide reversed some of this radiation-induced effect. As shown in FIG. 13B, the mean villus height in irradiated BALB/c and A/J mice treated with (D-Ala)-p2TA-(D-Ala) peptide was elevated to $141\pm27$ μm and $176\pm42$ μm, respectively. (D-Ala)-p2TA-(D-Ala) peptide had little or no effect on villus height in sham-irradiated mice.

Cyclin D1 expression is a marker for cell proliferation in jejunal crypts, and is critical for the maintenance of tissue homeostasis. While gastrointestinal (GI) samples from irradiated mice showed a marked decline in numbers of cyclin D1 positive cells (determined as described above), as demonstrated in FIG. 14, this decline was negligible in both BALB/c and A/J mice that had received the (D-Ala)-p2TA-(D-Ala) peptide 24 hours after the 8Gy irradiation. FIG. 14 demonstrates a weak cyclin D1 staining observed in a tissue of the R group (namely FIG. 14C and FIG. 14G for BALB/c and A/J mice, respectively) that is restored in the RP group of mice that received 5 mg/kg of (D-Ala)-p2TA-(D-Ala) peptide 24 h after irradiation (namely FIG. 14D and FIG. 14H for BALB/c and A/J mice, respectively).

Example 9 p2TA Peptide Inhibits Radiation-Induced Over-Expression of the Inflammatory Marker COX-2 in Jejunal Crypts and Spleen Cyclooxygenase-2 (COX-2) is a key inducible enzyme involved in prostaglandin production; it is generally undetectable in unperturbed epithelial tissues but can be strongly up-regulated by a number of inflammatory stimuli, including ionizing radiation (17). FIG. 15 and FIG. 16 show representative microphotographs of jejunum and spleen tissues, respectively, immuno-stained for COX-2 protein. Seven days after exposure to a radiation of 8 Gy, the jejunum (FIG. 15) and spleen (FIG. 16) demonstrated a marked increase in the expression of COX-2. Remarkably, a single administration of (D-Ala)-p2TA-(D-Ala) peptide 24 hours after radiation exposure ameliorated this radiation effect in all three tissues tested.

Example 10

Macrophage Recruitment to Small Intestine

Increased presence of macrophages in irradiates tissues has been noted and associated with inflammatory response of tissues to ionizing radiation. The activated macrophage marker F4/80 (26) was used for immunohistochemical staining of small intestine cross sections. As shown in FIG. 17, samples from irradiated mice displayed increased presence of F4/80-positive cells, from 3.39+1.08 cells/mm2 in controls to 6.69+3.20 cells/mm2 in irradiated BALB/c mice (not a significant difference, C vs. R group) and from 1.04+0.52 cells/mm2 in controls to 3.68+1.84 cells/mm2 in irradiated A/J mice (P<0.05, C vs. R group). However, (D-Ala)-p2TA-(D-Ala) treated irradiated animals displayed decreased numbers of F4/80-positive cells in both strains of mice. The number of macrophages in RP group was 0.77+0.31 cells/mm2 (P<0.05, R vs. RP group) in BALB/c mice and 1.37+0.68 cells/mm2 (P<0.05, R vs. RP group) in A/J mice. Therefore, a single administration of p2TA peptide 24 hours after exposure to radiation compensated for radiation-induced increase in macrophage recruitment to mouse intestine.

The invention claimed is:

1. A method for inhibiting radiation-induced or drug-induced inflammation in a human subject in need thereof, said method comprising administering to said subject a therapeutically effective amount of an isolated peptide which specifically binds to CD28, or a pharmaceutical composition comprising the same, wherein said isolated peptide is
   (a) selected from the group consisting of the amino acid sequences His Val Lys Gly Lys His Leu Cys Pro (designated p1TA as denoted by SEQ ID NO: 3), Ser Pro Met Leu Val Ala Tyr Asp (designated p2TA as denoted by SEQ ID NO: 4), His Lys Gly Leu Asp Ser Ala Val (designated p3TA as denoted by SEQ ID NO: 5), Tyr Val Asn Gln Thr Asp Ile Tyr (designated p4TA as denoted by SEQ ID NO:6), Asn Gly Thr Ile His Val Lys Gly (designated p5TA as denoted by SEQ ID NO: 7), Tyr Val Ile Asp Pro Glu Pro Cys Pro (designated p1TB as denoted by SEQ ID NO: 8), Pro Ala Val Val Leu Ala Ser Ser (designated p2 TB as denoted by SEQ ID NO: 9), Ser His Phe Thr His Asn Arg His Gly His Ser Thr (designated pe12 as denoted by SEQ ID NO: 12, or
   (b) a functional derivative of a peptide of (a), wherein said functional derivative maintains the ability to specifically bind to the CD28 homodimer interface and to inhibit said radiation-induced or drug-induced inflammation, said functional derivatives being selected from the group consisting of:
      (i) a peptide of (a) that has a substitution at one or more amino acid residues, each of which being a conservative amino acid replacement, the functional derivative with said substitution(s) maintaining at least 80% homology to the corresponding peptide of (a);
      (ii) a peptide of (a) or (b)(1) that is extended at the N terminus and/or the C terminus
         (1) by a lauryl cysteine at the N terminus and a cysteine at the C terminus; or
         (2) by an organic moiety that is not a naturally occurring or synthetic amino acid residue; or
         (3) by identical hydrophobic amino acid residue(s) which may be naturally occurring or synthetic amino acid residues; or
         (4) by a palmitoyl-lysine tail, wherein said tail is at the N terminus; and
      (iii) a peptide of (a) that is p1TA, p2TA, p3TA, p4TA or p5TA that is extended at the N-terminus and/or C-terminus thereof with 1-3 consecutive amino acid residues present in corresponding adjacent positions of the amino acid sequence of SEQ ID NO:1, or a peptide of (a) that is p1TB or p2 TB that is extended at the N-terminus and/or C-terminus thereof with 1-3 consecutive amino acid residues present in corresponding adjacent positions of the amino acid sequence of SEQ ID NO:2.

2. The method according to claim 1, wherein said isolated peptide is the amino acid sequence Ser Pro Met Leu Val Ala Tyr Asp denoted by SEQ ID NO: 4 (designated p2TA) or, as a functional derivative of said p2TA, the amino acid sequence (D-Ala) Ser Pro Met Leu Val Ala Tyr Asp (D-Ala) denoted by SEQ ID NO: 47 (designated (D-A)-p2TA-(D-A).

3. The method according to claim 1, wherein said isolated peptide comprises the amino acid sequence Pro Ala Val Leu Ala Ser (designated p2 TB as denoted by SEQ ID NO: 9), or, as functional derivatives of said p2 TB, (D-Ala)PAVV-LASS(D-Ala) (designated (D-A)-p2 TB-(D-A) as denoted by SEQ ID NO: 48) and or (palmitoyl-lysine) Pro Ala Val Leu Ala Ser (D-Ala) (designated (pal)-p2 TB-(D-A) as denoted by SEQ ID NO: 50).

4. The method according to claim 1, wherein said isolated peptide is a peptide consisting of the amino acid sequence Ser His Phe Thr His Asn Arg His Gly His Ser Thr (designated pe12 as denoted by SEQ ID NO: 12), or as functional derivatives of said pe12, (D-Ala) Ser His Phe Thr His Asn Arg His Gly His Ser Thr (D-Ala) (designated pe12-(D-A) as denoted by SEQ ID NO: 49) or (palmitoyl-lysine) Ser His Phe Thr His Asn Arg His Gly His Ser Thr D-Ala) (designated pe12-pal as denoted by SEQ ID NO: 51).

5. The method according to claim 1, wherein said radiation-induced or drug-induced inflammation is drug-induced inflammation that is drug-induced hepatitis, drug-induced ocular inflammation, drug-induced gastrointestinal damage, drug-induced acute ulcers, drug-induced renal failure, drug-induced pancreatitis, drug-induced nephritis, or chemotherapy-induced inflammation in the gastrointestinal tract.

6. The method according to claim 1, wherein said radiation-induced or drug-induced inflammation is-radiation-induced inflammation that is systemic and/or at the irradiated site.

7. The method according to claim 6, wherein said radiation-induced inflammation is associated with at least one of gastrointestinal tract and spleen inflammation.

8. The method according to claim 6, wherein said isolated peptide comprises the amino acid sequence Ser Pro Met Leu Val Ala Tyr Asp denoted by SEQ ID NO: 4 or, as a functional derivative thereof, the amino acid sequence (D-Ala) Ser Pro Met Leu Val Ala Tyr Asp (D-Ala) denoted by SEQ ID NO: 47.

9. The method according to claim 1, wherein said isolated peptide or pharmaceutical composition is administered by a route selected from the group consisting of intravenous, intramuscular or intraperitoneal administration, intrathecal or subcutaneous injection, oral, intrarectal, intranasal ocular and topical administration.

10. The method according to claim 1, wherein said isolated peptide is administered at an amount of from about 0.05 mg to about 5.0 mg peptide/kg body weight of a subject in need thereof.

11. The method according to claim 1, wherein said method comprises a single administration of said therapeutically effective dose of said isolated peptide or pharmaceutical composition.

12. The method according to claim 1, wherein said method comprises administering said therapeutically effective dose of said isolated peptide or pharmaceutical composition during one or more identical or different treatment periods of one, two, three or four weeks at a single daily administration, or at a single administration every three days, every five days or every seven days, wherein said treatment periods are consecutive or are set apart from each other by non-treatment intervals of 1 or several days, or 1 or several weeks or 1 or more months.

13. The method according to claim 1, wherein said isolated peptide or pharmaceutical composition is for chronic administration, optionally a single daily administration, or a single administration every three days, every five days or every seven days.

14. The method according to claim 1, wherein said administration is chronic administration.

15. The method according to claim 1, wherein said administering step comprises administering said isolated peptide or pharmaceutical composition comprising the same to said subject at a suitable time prior to and/or post irradiation, within about 24 hours following exposure to said radiation, or within from about 30 minutes up to any time at which the radiation-induced inflammation persists, whether while the subject is still undergoing radiation therapy, is in between radiation therapy treatments or after said radiation therapy.

16. The method according to claim 1, wherein said isolated peptide or pharmaceutical composition is administered in combination with at least one additional therapeutically active agent, which may be administered simultaneously, or at different time points, in any order, in identical or different frequencies, for identical or different durations of time.

17. The method according to claim 16, wherein said additional therapeutically active agent is a steroid, a non-steroidal anti-inflammatory agent or an immunosuppressive agent.

18. The method according to claim 16, wherein said subject in need suffers from radiation-induced gastroenteritis and wherein said at least one additional therapeutically active agent is a chemotherapeutic agent, a steroid or a non-steroidal anti-inflammatory agent.

19. The method according to claim 13, wherein said chronic administration comprises a single daily administration, or a single administration every three days, every five days or every seven days.

20. The method according to claim 6, wherein said radiation-induced inflammation is radiation-induced gastroenteritis.

21. The method according to claim 1, wherein said isolated peptide is a peptide of (a) extended at the N-terminus and/or the C-terminus by one or more D-Ala residues.

22. The method according to claim 1, wherein said isolated peptide is a peptide of (a) extended at the N-terminus by a palmitoyl-lysine tail.

* * * * *

```
                        SEQUENCE LISTING

<160> NUMBER OF SEQ ID NOS: 58

<210> SEQ ID NO 1
<211> LENGTH: 202
<212> TYPE: PRT
<213> ORGANISM: Homo sapiens

<400> SEQUENCE: 1

Asn Lys Ile Leu Val Lys Gln Ser Pro Met Leu Val Ala Tyr Asp Asn
1               5                   10                  15

Ala Val Asn Leu Ser Cys Lys Tyr Ser Tyr Asn Leu Phe Ser Arg Glu
            20                  25                  30

Phe Arg Ala Ser Leu His Lys Gly Leu Asp Ser Ala Val Glu Val Cys
        35                  40                  45

Val Val Tyr Gly Asn Tyr Ser Gln Gln Leu Gln Val Tyr Ser Lys Thr
    50                  55                  60

Gly Phe Asn Cys Asp Gly Lys Leu Gly Asn Glu Ser Val Thr Phe Tyr
65                  70                  75                  80

Leu Gln Asn Leu Tyr Val Asn Gln Thr Asp Ile Tyr Phe Cys Lys Ile
                85                  90                  95

Glu Val Met Tyr Pro Pro Pro Tyr Leu Asp Asn Glu Lys Ser Asn Gly
            100                 105                 110

Thr Ile Ile His Val Lys Gly Lys His Leu Cys Pro Ser Pro Leu Phe
        115                 120                 125

Pro Gly Pro Ser Lys Pro Phe Trp Val Leu Val Val Val Gly Gly Val
    130                 135                 140

Leu Ala Cys Tyr Ser Leu Leu Val Thr Val Ala Phe Ile Ile Phe Trp
145                 150                 155                 160

Val Arg Ser Lys Arg Ser Arg Leu Leu His Ser Asp Tyr Met Asn Met
                165                 170                 175

Thr Pro Arg Arg Pro Gly Pro Thr Arg Lys His Tyr Gln Pro Tyr Ala
            180                 185                 190

Pro Pro Arg Asp Phe Ala Ala Tyr Arg Ser
        195                 200

<210> SEQ ID NO 2
<211> LENGTH: 188
<212> TYPE: PRT
<213> ORGANISM: Homo sapiens

<400> SEQUENCE: 2

Lys Ala Met His Val Ala Gln Pro Ala Val Val Leu Ala Ser Ser Arg
1               5                   10                  15

Gly Ile Ala Ser Phe Val Cys Glu Tyr Ala Ser Pro Gly Lys Ala Thr
            20                  25                  30
```

```
Glu Val Arg Val Thr Val Leu Arg Gln Ala Asp Ser Gln Val Thr Glu
            35                  40                  45

Val Cys Ala Ala Thr Tyr Met Met Gly Asn Glu Leu Thr Phe Leu Asp
 50                  55                  60

Asp Ser Ile Cys Thr Gly Thr Ser Ser Gly Asn Gln Val Asn Leu Thr
 65                  70                  75                  80

Ile Gln Gly Leu Arg Ala Met Asp Thr Gly Leu Tyr Ile Cys Lys Val
                 85                  90                  95

Glu Leu Met Tyr Pro Pro Pro Tyr Leu Gly Ile Gly Asn Gly Thr
            100                 105                 110

Gln Ile Tyr Val Ile Asp Pro Glu Pro Cys Pro Asp Ser Asp Phe Leu
            115                 120                 125

Leu Trp Ile Leu Ala Ala Val Ser Ser Gly Leu Phe Phe Tyr Ser Phe
            130                 135                 140

Leu Leu Thr Ala Val Ser Leu Ser Lys Met Leu Lys Lys Arg Ser Pro
145                 150                 155                 160

Leu Thr Thr Gly Val Tyr Val Lys Met Pro Pro Thr Glu Pro Glu Cys
                165                 170                 175

Glu Lys Gln Phe Gln Pro Tyr Phe Ile Pro Ile Asn
            180                 185

<210> SEQ ID NO 3
<211> LENGTH: 9
<212> TYPE: PRT
<213> ORGANISM: Artificial Sequence
<220> FEATURE:
<223> OTHER INFORMATION: Synthetic peptide p1TA

<400> SEQUENCE: 3

His Val Lys Gly Lys His Leu Cys Pro
1               5

<210> SEQ ID NO 4
<211> LENGTH: 8
<212> TYPE: PRT
<213> ORGANISM: Artificial Sequence
<220> FEATURE:
<223> OTHER INFORMATION: Synthetic peptide p2TA

<400> SEQUENCE: 4

Ser Pro Met Leu Val Ala Tyr Asp
1               5

<210> SEQ ID NO 5
<211> LENGTH: 8
<212> TYPE: PRT
<213> ORGANISM: Artificial Sequence
<220> FEATURE:
<223> OTHER INFORMATION: Synthetic peptide p3TA

<400> SEQUENCE: 5

His Lys Gly Leu Asp Ser Ala Val
1               5

<210> SEQ ID NO 6
<211> LENGTH: 8
<212> TYPE: PRT
<213> ORGANISM: Artificial Sequence
<220> FEATURE:
<223> OTHER INFORMATION: synthetic peptide p4TA
```

```
<400> SEQUENCE: 6

Tyr Val Asn Gln Thr Asp Ile Tyr
1               5

<210> SEQ ID NO 7
<211> LENGTH: 9
<212> TYPE: PRT
<213> ORGANISM: Artificial Sequence
<220> FEATURE:
<223> OTHER INFORMATION: synthetic peptide p5TA

<400> SEQUENCE: 7

Asn Gly Thr Ile Ile His Val Lys Gly
1               5

<210> SEQ ID NO 8
<211> LENGTH: 9
<212> TYPE: PRT
<213> ORGANISM: Artificial Sequence
<220> FEATURE:
<223> OTHER INFORMATION: synthetic peptide p1TB

<400> SEQUENCE: 8

Tyr Val Ile Asp Pro Glu Pro Cys Pro
1               5

<210> SEQ ID NO 9
<211> LENGTH: 8
<212> TYPE: PRT
<213> ORGANISM: Artificial Sequence
<220> FEATURE:
<223> OTHER INFORMATION: synthetic peptide p2TB

<400> SEQUENCE: 9

Pro Ala Val Val Leu Ala Ser Ser
1               5

<210> SEQ ID NO 10
<211> LENGTH: 12
<212> TYPE: PRT
<213> ORGANISM: Artificial Sequence
<220> FEATURE:
<223> OTHER INFORMATION: synthetic peptide p12A

<400> SEQUENCE: 10

Tyr Asn Lys Lys Lys Ala Thr Val Gln Glu Leu Asp
1               5                   10

<210> SEQ ID NO 11
<211> LENGTH: 14
<212> TYPE: PRT
<213> ORGANISM: Artificial Sequence
<220> FEATURE:
<223> OTHER INFORMATION: synthetic peptide p12B

<400> SEQUENCE: 11

Val Gln Tyr Asn Lys Lys Lys Ala Thr Val Gln Glu Leu Asp
1               5                   10

<210> SEQ ID NO 12
<211> LENGTH: 12
<212> TYPE: PRT
<213> ORGANISM: Artificial Sequence
<220> FEATURE:
<223> OTHER INFORMATION: Synthetic
<220> FEATURE:
<223> OTHER INFORMATION: core sequence pe 12
```

```
<400> SEQUENCE: 12

Ser His Phe Thr His Asn Arg His Gly His Ser Thr
1               5                   10

<210> SEQ ID NO 13
<211> LENGTH: 12
<212> TYPE: PRT
<213> ORGANISM: Artificial Sequence
<220> FEATURE:
<223> OTHER INFORMATION: synthetic peptide pd7

<400> SEQUENCE: 13

Trp His Ala His Pro His Lys Lys Pro Val Val Ala
1               5                   10

<210> SEQ ID NO 14
<211> LENGTH: 11
<212> TYPE: PRT
<213> ORGANISM: Artificial Sequence
<220> FEATURE:
<223> OTHER INFORMATION: synthetic peptide pc3

<400> SEQUENCE: 14

His Lys His Lys Asn Pro Gly Ser Pro Ile Ile
1               5                   10

<210> SEQ ID NO 15
<211> LENGTH: 12
<212> TYPE: PRT
<213> ORGANISM: Artificial Sequence
<220> FEATURE:
<223> OTHER INFORMATION: synthetic peptide pa2

<400> SEQUENCE: 15

Phe His Lys His Ser Pro Arg Ser Pro Ile Phe Ile
1               5                   10

<210> SEQ ID NO 16
<211> LENGTH: 12
<212> TYPE: PRT
<213> ORGANISM: Artificial Sequence
<220> FEATURE:
<223> OTHER INFORMATION: synthetic peptide pb4

<400> SEQUENCE: 16

Ser Trp Pro His His His Arg Met Pro Leu Leu Ala
1               5                   10

<210> SEQ ID NO 17
<211> LENGTH: 12
<212> TYPE: PRT
<213> ORGANISM: Artificial Sequence
<220> FEATURE:
<223> OTHER INFORMATION: synthetic pc11

<400> SEQUENCE: 17

Phe His Lys Thr Pro Arg Ile Ala Pro Pro Pro Leu
1               5                   10

<210> SEQ ID NO 18
<211> LENGTH: 12
<212> TYPE: PRT
<213> ORGANISM: Artificial Sequence
<220> FEATURE:
<223> OTHER INFORMATION: synthetic peptide pf11
```

```
<400> SEQUENCE: 18

His Ser Ser His His Ser His Arg Ala Pro Thr Thr
1               5                   10

<210> SEQ ID NO 19
<211> LENGTH: 12
<212> TYPE: PRT
<213> ORGANISM: Artificial Sequence
<220> FEATURE:
<223> OTHER INFORMATION: synthetic pg3

<400> SEQUENCE: 19

His Asn Ser Tyr His His Gln His Lys Pro Thr Ser
1               5                   10

<210> SEQ ID NO 20
<211> LENGTH: 12
<212> TYPE: PRT
<213> ORGANISM: Artificial Sequence
<220> FEATURE:
<223> OTHER INFORMATION: synthetic peptide pb12

<400> SEQUENCE: 20

Tyr His Arg Pro His Glu His Lys Met Phe Gln Pro
1               5                   10

<210> SEQ ID NO 21
<211> LENGTH: 12
<212> TYPE: PRT
<213> ORGANISM: Artificial Sequence
<220> FEATURE:
<223> OTHER INFORMATION: synthetic peptide pa8.1

<400> SEQUENCE: 21

Ala His Lys Ala His Lys His Met Pro Trp Ile Asn
1               5                   10

<210> SEQ ID NO 22
<211> LENGTH: 12
<212> TYPE: PRT
<213> ORGANISM: Artificial Sequence
<220> FEATURE:
<223> OTHER INFORMATION: synthetic peptide  pb3

<400> SEQUENCE: 22

Ala Pro Trp Thr His His Ser Lys His Ser His Pro
1               5                   10

<210> SEQ ID NO 23
<211> LENGTH: 12
<212> TYPE: PRT
<213> ORGANISM: Artificial Sequence
<220> FEATURE:
<223> OTHER INFORMATION: synthetic peptide pb5

<400> SEQUENCE: 23

Lys Pro Phe His His Asp His Ser Lys Gln His Gln
1               5                   10

<210> SEQ ID NO 24
<211> LENGTH: 12
<212> TYPE: PRT
<213> ORGANISM: Artificial Sequence
<220> FEATURE:
<223> OTHER INFORMATION: synthetic peptide  pc5
```

```
<400> SEQUENCE: 24

Ala Arg Leu His Thr His Gln His Ser Asn Met Arg
1               5                   10

<210> SEQ ID NO 25
<211> LENGTH: 12
<212> TYPE: PRT
<213> ORGANISM: Artificial Sequence
<220> FEATURE:
<223> OTHER INFORMATION: synthetic peptide pf3

<400> SEQUENCE: 25

Gly Gln Thr His His His His Arg Phe Phe Gly Ser
1               5                   10

<210> SEQ ID NO 26
<211> LENGTH: 12
<212> TYPE: PRT
<213> ORGANISM: Artificial Sequence
<220> FEATURE:
<223> OTHER INFORMATION: synthetic peptide pf8

<400> SEQUENCE: 26

Ile His Lys Pro His His His Arg Thr Pro Leu Trp
1               5                   10

<210> SEQ ID NO 27
<211> LENGTH: 12
<212> TYPE: PRT
<213> ORGANISM: Artificial Sequence
<220> FEATURE:
<223> OTHER INFORMATION: synthetic peptide pe6

<400> SEQUENCE: 27

Ala Pro Met Tyr His Lys His Arg Leu Glu Lys His
1               5                   10

<210> SEQ ID NO 28
<211> LENGTH: 12
<212> TYPE: PRT
<213> ORGANISM: Artificial Sequence
<220> FEATURE:
<223> OTHER INFORMATION: synthetic peptide pf4

<400> SEQUENCE: 28

Trp His Lys Ile Pro Gln Lys Ala Pro Leu Asn Pro
1               5                   10

<210> SEQ ID NO 29
<211> LENGTH: 12
<212> TYPE: PRT
<213> ORGANISM: Artificial Sequence
<220> FEATURE:
<223> OTHER INFORMATION: synthetic peptide  pa8.2

<400> SEQUENCE: 29

Tyr Pro His Ile His Thr His Arg Pro Pro Val His
1               5                   10

<210> SEQ ID NO 30
<211> LENGTH: 12
<212> TYPE: PRT
<213> ORGANISM: Artificial Sequence
<220> FEATURE:
<223> OTHER INFORMATION: synthetic peptide b7
```

```
<400> SEQUENCE: 30

Ala Trp Asn Ser Pro His Gln His His Arg Lys
1               5                   10

<210> SEQ ID NO 31
<211> LENGTH: 12
<212> TYPE: PRT
<213> ORGANISM: Artificial Sequence
<220> FEATURE:
<223> OTHER INFORMATION: synthetic peptide pb2

<400> SEQUENCE: 31

Trp Pro Arg His His His Ser Gly Glu Leu Lys Thr
1               5                   10

<210> SEQ ID NO 32
<211> LENGTH: 12
<212> TYPE: PRT
<213> ORGANISM: Artificial Sequence
<220> FEATURE:
<223> OTHER INFORMATION: synthatic peptide  pc2

<400> SEQUENCE: 32

Ser His Trp His Ser Lys Leu Arg Tyr Phe Pro Pro
1               5                   10

<210> SEQ ID NO 33
<211> LENGTH: 12
<212> TYPE: PRT
<213> ORGANISM: Artificial Sequence
<220> FEATURE:
<223> OTHER INFORMATION: synthetic peptide  pc8

<400> SEQUENCE: 33

Leu Pro His His Lys His Arg Pro Asn Leu Pro Ser
1               5                   10

<210> SEQ ID NO 34
<211> LENGTH: 12
<212> TYPE: PRT
<213> ORGANISM: Artificial Sequence
<220> FEATURE:
<223> OTHER INFORMATION: synthetic peptide pc9

<400> SEQUENCE: 34

Phe His Lys His Asn Tyr Lys Ser Pro Pro Ile Ile
1               5                   10

<210> SEQ ID NO 35
<211> LENGTH: 12
<212> TYPE: PRT
<213> ORGANISM: Artificial Sequence
<220> FEATURE:
<223> OTHER INFORMATION: synthetic peptide pf 12

<400> SEQUENCE: 35

Trp Pro Met Lys His His His Leu Val Thr Ala Arg
1               5                   10

<210> SEQ ID NO 36
<211> LENGTH: 12
<212> TYPE: PRT
<213> ORGANISM: Artificial Sequence
<220> FEATURE:
<223> OTHER INFORMATION: synthetic peptide pc4
```

```
<400> SEQUENCE: 36

His Ile Lys His Leu Ser His Trp Thr Pro Lys Pro
1               5                   10

<210> SEQ ID NO 37
<211> LENGTH: 12
<212> TYPE: PRT
<213> ORGANISM: Artificial Sequence
<220> FEATURE:
<223> OTHER INFORMATION: synthetic peptide pe11

<400> SEQUENCE: 37

Ala His Arg His Gln His Gln His Pro His Ala Gln
1               5                   10

<210> SEQ ID NO 38
<211> LENGTH: 12
<212> TYPE: PRT
<213> ORGANISM: Artificial Sequence
<220> FEATURE:
<223> OTHER INFORMATION: synthetic peptide pb5

<400> SEQUENCE: 38

Leu Pro Trp His Arg His Gly Pro Ala Pro Ser Phe
1               5                   10

<210> SEQ ID NO 39
<211> LENGTH: 12
<212> TYPE: PRT
<213> ORGANISM: Artificial Sequence
<220> FEATURE:
<223> OTHER INFORMATION: synthetic peptide pe13

<400> SEQUENCE: 39

Ala Pro Trp Ser His His His Gly Lys Leu Pro Arg
1               5                   10

<210> SEQ ID NO 40
<211> LENGTH: 12
<212> TYPE: PRT
<213> ORGANISM: Artificial Sequence
<220> FEATURE:
<223> OTHER INFORMATION: synthetic peptide pg7

<400> SEQUENCE: 40

Gly Leu Trp His Ala Pro His Pro Ala His Arg His
1               5                   10

<210> SEQ ID NO 41
<211> LENGTH: 12
<212> TYPE: PRT
<213> ORGANISM: Artificial Sequence
<220> FEATURE:
<223> OTHER INFORMATION: synthetic peptide pa12

<400> SEQUENCE: 41

Thr Gln Gly His His His His Arg His Pro Arg Ile
1               5                   10

<210> SEQ ID NO 42
<211> LENGTH: 12
<212> TYPE: PRT
<213> ORGANISM: Artificial Sequence
<220> FEATURE:
<223> OTHER INFORMATION: synthetic peptide pb 8
```

```
<400> SEQUENCE: 42

Ser Pro His Asn His Thr His Lys Pro Lys Ser
1               5                   10

<210> SEQ ID NO 43
<211> LENGTH: 12
<212> TYPE: PRT
<213> ORGANISM: Artificial Sequence
<220> FEATURE:
<223> OTHER INFORMATION: synthetic peptide pb 12

<400> SEQUENCE: 43

Leu Pro Met Lys His Ser Trp His Ser His Thr Leu
1               5                   10

<210> SEQ ID NO 44
<211> LENGTH: 12
<212> TYPE: PRT
<213> ORGANISM: Artificial Sequence
<220> FEATURE:
<223> OTHER INFORMATION: synthetic peptide pc 8

<400> SEQUENCE: 44

Ala Val Lys His His Tyr His Arg His Pro Ile Ile
1               5                   10

<210> SEQ ID NO 45
<211> LENGTH: 12
<212> TYPE: PRT
<213> ORGANISM: Artificial Sequence
<220> FEATURE:
<223> OTHER INFORMATION: synthetic peptide pd 8

<400> SEQUENCE: 45

Thr His Pro His Leu His His Arg His Leu Ala Pro
1               5                   10

<210> SEQ ID NO 46
<211> LENGTH: 12
<212> TYPE: PRT
<213> ORGANISM: Artificial Sequence
<220> FEATURE:
<223> OTHER INFORMATION: synthetic peptide pg 6

<400> SEQUENCE: 46

Gly Lys Met His Leu His His Pro His Ser Gln Pro
1               5                   10

<210> SEQ ID NO 47
<211> LENGTH: 10
<212> TYPE: PRT
<213> ORGANISM: Artificial Sequence
<220> FEATURE:
<223> OTHER INFORMATION: synthetic peptide p2TA
<220> FEATURE:
<221> NAME/KEY: MISC_FEATURE
<222> LOCATION: (1)..(10)
<223> OTHER INFORMATION: Xaa is equal to D-Alanine

<400> SEQUENCE: 47

Xaa Ser Pro Met Leu Val Ala Tyr Asp Xaa
1               5                   10

<210> SEQ ID NO 48
<211> LENGTH: 10
<212> TYPE: PRT
<213> ORGANISM: Artificial Sequence
```

```
<220> FEATURE:
<223> OTHER INFORMATION: synthetic peptide p2 TB
<220> FEATURE:
<221> NAME/KEY: MISC_FEATURE
<222> LOCATION: (1)..(10)
<223> OTHER INFORMATION: Xaa is equal to D-Alanine

<400> SEQUENCE: 48

Xaa Pro Ala Val Val Leu Ala Ser Ser Xaa
1               5                   10

<210> SEQ ID NO 49
<211> LENGTH: 14
<212> TYPE: PRT
<213> ORGANISM: Artificial Sequence
<220> FEATURE:
<223> OTHER INFORMATION: synthetic peptide pe 12
<220> FEATURE:
<221> NAME/KEY: MISC_FEATURE
<222> LOCATION: (1)..(14)
<223> OTHER INFORMATION: Xaa is equal to D-Alanine

<400> SEQUENCE: 49

Xaa Ser His Phe Thr His Asn Arg His Gly His Ser Thr Xaa
1               5                   10

<210> SEQ ID NO 50
<211> LENGTH: 8
<212> TYPE: PRT
<213> ORGANISM: Artificial Sequence
<220> FEATURE:
<223> OTHER INFORMATION: synthetic peptide p2TB-pal

<400> SEQUENCE: 50

Pro Ala Val Val Leu Ala Ser Ser
1               5

<210> SEQ ID NO 51
<211> LENGTH: 12
<212> TYPE: PRT
<213> ORGANISM: Artificial Sequence
<220> FEATURE:
<223> OTHER INFORMATION: synthetic peptide pe 12-pal

<400> SEQUENCE: 51

Ser His Phe Thr His Asn Arg His Gly His Ser Thr
1               5                   10

<210> SEQ ID NO 52
<211> LENGTH: 10
<212> TYPE: PRT
<213> ORGANISM: Artificial Sequence
<220> FEATURE:
<223> OTHER INFORMATION: Synthetic
<220> FEATURE:
<223> OTHER INFORMATION: scrambelled peptide p2TAsc
<220> FEATURE:
<221> NAME/KEY: MISC_FEATURE
<222> LOCATION: (1)..(8)
<223> OTHER INFORMATION: Xaa is equal to D-Alanine
<220> FEATURE:
<221> NAME/KEY: misc_feature
<222> LOCATION: (10)..(10)
<223> OTHER INFORMATION: Xaa can be any naturally occurring amino acid

<400> SEQUENCE: 52

Xaa Ala Ser Met Asp Tyr Pro Val Leu Xaa
1               5                   10
```

```
<210> SEQ ID NO 53
<211> LENGTH: 27
<212> TYPE: PRT
<213> ORGANISM: Artificial Sequence
<220> FEATURE:
<223> OTHER INFORMATION: Synthetic
<220> FEATURE:
<223> OTHER INFORMATION: PCR primer

<400> SEQUENCE: 53

Gly Ala Cys Gly Thr Cys Gly Ala Cys Gly Gly Ala Ala Gly Gly Cys
1               5                   10                  15

Thr Thr Gly Cys Ala Cys Ala Gly Gly Gly Thr
            20                  25

<210> SEQ ID NO 54
<211> LENGTH: 32
<212> TYPE: PRT
<213> ORGANISM: Artificial Sequence
<220> FEATURE:
<223> OTHER INFORMATION: Synthetic
<220> FEATURE:
<223> OTHER INFORMATION: PCR primer

<400> SEQUENCE: 54

Cys Ala Cys Gly Cys Gly Gly Cys Cys Gly Cys Cys Cys Ala Gly Gly
1               5                   10                  15

Thr Cys Ala Thr Gly Ala Gly Cys Cys Ala Thr Thr Ala Ala Gly Cys
            20                  25                  30

<210> SEQ ID NO 55
<211> LENGTH: 27
<212> TYPE: PRT
<213> ORGANISM: Artificial Sequence
<220> FEATURE:
<223> OTHER INFORMATION: Synthetic
<220> FEATURE:
<223> OTHER INFORMATION: PCR primer

<400> SEQUENCE: 55

Thr Ala Cys Thr Cys Gly Ala Gly Ala Thr Gly Gly Gly Ala Cys Thr
1               5                   10                  15

Gly Ala Gly Thr Ala Ala Cys Ala Thr Thr Cys
            20                  25

<210> SEQ ID NO 56
<211> LENGTH: 30
<212> TYPE: PRT
<213> ORGANISM: Artificial Sequence
<220> FEATURE:
<223> OTHER INFORMATION: Synthetic
<220> FEATURE:
<223> OTHER INFORMATION: PCR primer

<400> SEQUENCE: 56

Gly Thr Cys Cys Gly Cys Gly Gly Thr Gly Ala Ala Gly Cys Ala Thr
1               5                   10                  15

Gly Thr Ala Cys Ala Cys Thr Thr Thr Thr Gly Thr Cys Gly
            20                  25                  30

<210> SEQ ID NO 57
<211> LENGTH: 17
<212> TYPE: PRT
<213> ORGANISM: Artificial Sequence
<220> FEATURE:
<223> OTHER INFORMATION: Synthetic
```

```
-continued

<220> FEATURE:
<223> OTHER INFORMATION: PCR primer

<400> SEQUENCE: 57

Gly Thr Cys Thr Cys Thr Cys Gly Thr Cys Cys Thr Cys Cys Gly
1               5                   10                  15

Gly

<210> SEQ ID NO 58
<211> LENGTH: 18
<212> TYPE: PRT
<213> ORGANISM: Artificial Sequence
<220> FEATURE:
<223> OTHER INFORMATION: Synthetic
<220> FEATURE:
<223> OTHER INFORMATION: PCR primer

<400> SEQUENCE: 58

Cys Thr Ala Ala Cys Thr Thr Cys Ala Gly Thr Cys Ala Ala Cys Cys
1               5                   10                  15

Thr Gly
```